United States Patent
Pless

(10) Patent No.: US 7,089,059 B1
(45) Date of Patent: Aug. 8, 2006

(54) PREDICTING SUSCEPTIBILITY TO NEUROLOGICAL DYSFUNCTION BASED ON MEASURED NEURAL ELECTROPHYSIOLOGY

(76) Inventor: Benjamin D. Pless, 255 Santa Ana Ct., Atherton, CA (US) 94085

( * ) Notice: Subject to any disclaimer, the term of this patent is extended or adjusted under 35 U.S.C. 154(b) by 164 days.

(21) Appl. No.: 09/706,322

(22) Filed: Nov. 3, 2000

(51) Int. Cl.
*A61N 1/32* (2006.01)

(52) U.S. Cl. ............................................ 607/45

(58) Field of Classification Search .............. 607/45; 600/544, 545
See application file for complete search history.

(56) References Cited

U.S. PATENT DOCUMENTS

| 3,880,144 | A | * | 4/1975 | Coursin et al. | |
| 4,503,863 | A | * | 3/1985 | Katims | |
| 6,066,163 | A | * | 5/2000 | John | 607/45 |
| 6,463,328 | B1 | * | 10/2002 | John | 607/45 |

* cited by examiner

*Primary Examiner*—Scott M. Getzow

(57) ABSTRACT

A system and method for determining and predicting a patient's susceptibility to neurological dysfunction based on measured electrophysiological parameters employs a self-contained implantable device with depth electrodes implanted in desired locations in the patient's brain. The patient's neurological tissue is stimulated to determine excitability and refractoriness (or inhibition period) parameters, which are employed to identify susceptibility to abnormal neurological activity, particularly epileptic seizures.

17 Claims, 17 Drawing Sheets

PREDICTING SUSCEPTIBILITY TO NEUROLOGICAL DYSFUNCTION BASED ON MEASURED NEURAL ELECTROPHYSIOLOGY

FIELD OF THE INVENTION

The invention relates to systems and methods for measuring susceptibility to neurological dysfunction based on analysis of neural electrophysiology, and more particularly to a system and method for determining whether a patient suffering from epilepsy is particularly vulnerable to an imminent epileptic seizure based on periodic analysis of brain evoked response characteristics.

BACKGROUND OF THE INVENTION

Epilepsy, a neurological disorder characterized by the occurrence of seizures (specifically episodic impairment or loss of consciousness, abnormal motor phenomena, psychic or sensory disturbances, or the perturbation of the autonomic nervous system), is debilitating to a great number of people. It is believed that as many as two to four million Americans may suffer from various forms of epilepsy. Research has found that its prevalence may be even greater worldwide, particularly in less economically developed nations, suggesting that the worldwide figure for epilepsy sufferers may be in excess of one hundred million.

Because epilepsy is characterized by seizures, its sufferers are frequently limited in the kinds of activities they may participate in. Epilepsy can prevent people from driving, working, or otherwise participating in much of what society has to offer. Some epilepsy sufferers have serious seizures so frequently that they are effectively incapacitated.

Furthermore, epilepsy is often progressive and can be associated with degenerative disorders and conditions. Over time, epileptic seizures often become more frequent and more serious, and in particularly severe cases, are likely to lead to deterioration of other brain functions (including cognitive function) as well as physical impairments.

The current state of the art in treating neurological disorders, particularly epilepsy, typically involves drug therapy and surgery. The first approach is usually drug therapy.

A number of drugs are approved and available for treating epilepsy, such as sodium valproate, phenobarbital/primidone, ethosuximide, gabapentin, phenyloin, and carbamazepine, as well as a number of others. Unfortunately, those drugs typically have serious side effects, especially toxicity, and it is extremely important in most cases to maintain a precise therapeutic serum level to avoid breakthrough seizures (if the dosage is too low) or toxic effects (if the dosage is too high). The need for patient discipline is high, especially when a patient's drug regimen causes unpleasant side effects the patient may wish to avoid.

Moreover, while many patients respond well to drug therapy alone, a significant number (at least 20–30%) do not. For those patients, surgery is presently the best-established and most viable alternative course of treatment.

Currently practiced surgical approaches include radical surgical resection such as hemispherectomy, corticectomy, lobectomy and partial lobectomy, and less-radical lesionectomy, transection, and stereotactic ablation. Besides being less than fully successful, these surgical approaches generally have a high risk of complications, and can often result in damage to eloquent (i.e., functionally important) brain regions and the consequent long-term impairment of various cognitive and other neurological functions. Furthermore, for a variety of reasons, such surgical treatments are contraindicated in a substantial number of patients. And unfortunately, even after radical brain surgery, many epilepsy patients are still not seizure-free.

Electrical stimulation is an emerging therapy for treating epilepsy. However, currently approved and available electrical stimulation devices apply continuous electrical stimulation to neural tissue surrounding or near implanted electrodes, and do not perform any detection—they are not responsive to relevant neurological conditions.

The NeuroCybernetic Prosthesis (NCP) from Cyberonics, for example, applies continuous electrical stimulation to the patient's vagus nerve. This approach has been found to reduce seizures by about 50% in about 50% of patients. Unfortunately, a much greater reduction in the incidence of seizures is needed to provide clinical benefit. The Activa device from Medtronic is a pectorally implanted continuous deep brain stimulator intended primarily to treat Parkinson's disease. In operation, it supplies a continuous electrical pulse stream to a selected deep brain structure where an electrode has been implanted.

Continuous stimulation of deep brain structures for the treatment of epilepsy has not met with consistent success. To be effective in terminating seizures, it is believed that one effective site where stimulation should be performed is near the focus of the epileptogenic region. The focus is often in the neocortex, where continuous stimulation may cause significant neurological deficit with clinical symptoms including loss of speech, sensory disorders, or involuntary motion. Accordingly, research has been directed toward automatic responsive epilepsy treatment based on a detection of imminent seizure.

A typical epilepsy patient experiences episodic attacks or seizures, which are generally defined as periods of abnormal neurological activity. As is traditional in the art, such periods shall be referred to herein as "ictal" (though it should be noted that "ictal" can refer to neurological phenomena other than epileptic seizures).

Most prior work on the detection and responsive treatment of seizures via electrical stimulation has focused on analysis of electroencephalogram (EEG) and electrocorticogram (ECoG) waveforms. In general, EEG signals represent aggregate neuronal activity potentials detectable via electrodes applied to a patient's scalp, and ECoGs use internal electrodes on or near the brain. ECoG signals, deep-brain counterparts to EEG signals, are detectable via electrodes implanted under the dura mater, and sometimes within the patient's brain. Unless the context clearly and expressly indicates otherwise, the term "EEG" shall be used generically herein to refer to both EEG and ECoG signals.

Much of the work on detection has focused on the use of time-domain analysis of EEG signals. See, e.g., J. Gotman, Automatic seizure detection: improvements and evaluation, Electroencephalogr. Clin. Neurophysiol. 1990; 76(4): 317–24. In a typical time-domain detection system, EEG signals are received by one or more implanted electrodes and then processed by a control module, which then is capable of performing an action (intervention, warning, recording, etc.) when an abnormal event is detected.

In the Gotman system, EEG waveforms are filtered and decomposed into "features" representing characteristics of interest in the waveforms. One such feature is characterized by the regular occurrence (i.e., density) of half-waves exceeding a threshold amplitude occurring in a specified frequency band between approximately 3 Hz and 20 Hz, especially in comparison to background (non-ictal) activity. When such half-waves are detected, the onset of a seizure is identified.

A more computationally demanding approach is to transform EEG signals into the frequency domain for rigorous spectrum analysis. See, e.g., U.S. Pat. No. 5,995,868 to Dorfineister et al., which analyzes the power spectral density of EEG signals in comparison to background characteristics. Although this approach is generally believed to achieve good results, for the most part, its computational expense renders it less than optimal for use in long-term implanted epilepsy monitor and treatment devices. With current technology, the battery life in an implantable device computationally capable of performing the Dorfineister method would be too short for it to be feasible.

Also representing an alternative and more complex approach is U.S. Pat. No. 5,857,978 to Hively et al., in which various non-linear and statistical characteristics of EEG signals are analyzed to identify the onset of ictal activity. Once more, the calculation of statistically relevant characteristics is not believed to be feasible in an implantable device.

U.S. Pat. No. 6,016,449 to Fischell, et al. (which is hereby incorporated by reference as though set forth in full herein), describes an implantable seizure detection and treatment system. In the Fischell system, various detection methods are possible, all of which essentially rely upon the analysis (either in the time domain or the frequency domain) of processed EEG signals. Fischell's controller is preferably implanted intracranially, but other approaches are also possible, including the use of an external controller. When a seizure is detected, the Fischell system applies responsive electrical stimulation to terminate the seizure, a capability that will be discussed in further detail below.

All of these approaches provide useful information, and in some cases may provide sufficient information for accurate detection and prediction of most imminent epileptic seizures.

However, none of the various implementations of the known approaches provide 100% seizure detection accuracy in a clinical environment.

Two types of detection errors are generally possible. A "false positive," as the term is used herein, refers to a detection of a seizure or ictal activity when no seizure or other abnormal event is actually occurring. Similarly, a "false negative" herein refers to the failure to detect a seizure or ictal activity that actually is occurring or shortly will occur.

In most cases, with all known implementations of the known approaches to detecting abnormal seizure activity solely by monitoring and analyzing EEG activity, when a seizure detection algorithm is tuned to catch all seizures, there will be a significant number of false positives. While it is currently believed that there are minimal or no side effects to over-stimulation (e.g., providing stimulation sufficient to terminate a seizure in response to a false positive), the possibility of accidentally initiating a seizure must be considered.

Known systems for detecting epileptic seizures are essentially passive in nature (i.e., they receive and process existing signals), and valuable information about the physiological state of the brain is typically not available. Although most or nearly all seizures may be detected by a well-tuned system passive system according to the art, there may be a significant number of false-positive detections, and some seizures may not be detected early enough to facilitate successful treatment.

As is well known, it has been suggested that it is possible to treat and terminate seizures by applying electrical stimulation to the brain. See, e.g., U.S. Pat. No. 6,016,449 to Fischell et al., and H. R. Wagner, et al., Suppression of cortical epileptiform activity by generalized and localized ECoG desynchronization, Electroencephalogr. Clin. Neurophysiol. 1975; 39(5): 499–506. And as stated above, it is believed to be beneficial to perform this stimulation only when a seizure (or other undesired neurological event) is occurring or about to occur, as inappropriate stimulation may result in the initiation of seizures.

Furthermore, it should be noted that a false negative (that is, a seizure that occurs without any warning or treatment from the device) will often cause the patient significant discomfort and detriment. Clearly, false negatives are to be avoided.

To generalize, it is presently believed there may not be sufficient information in EEG waveforms to permit accurate detection and prediction of seizures in all cases. And if the information is present, it may be manifested in a way that makes it computationally difficult, if not impossible, to extract it from other EEG contents, such as normal brain activity and noise.

SUMMARY OF THE INVENTION

In contrast to the continuous brain stimulation systems described above and to seizure detection systems using only passive EEG information, the present invention performs an active analysis of neural electrophysiological parameters to identify susceptibility to imminent seizure activity.

In particular, an embodiment of the invention performs periodic active tests of brain tissue excitability and refractoriness (or inhibition) to determine whether hypersynchronous neuronal discharges, which are often characteristic of ictal activity, are more likely than usual to occur.

In a system and method according to the present invention, the measured parameters serve as predictors for seizure activity. These parameters can be used alone or in combination with the passive EEG-based detection methods described above, or others, to provide enhanced seizure detection and therapeutic capabilities.

In the disclosed embodiment, a system and method according to the invention utilizes an implantable control module and one or more brain electrodes to sense and record EEG signals, perform periodic active neural electrophysiological measurements, compare the signals and measurements to baseline or "normal" conditions (which may be undergo normal changes over time), and perform electrical stimulation (or take other actions) as necessary to terminate a seizure, reduce the likelihood of a seizure occurring, warn the patient that a seizure is about to occur, or record the abnormal activity. This measurement step is described as "active" herein because electrophysiological parameters are measured by providing occasional stimulation pulses to prompt a detectable evoked response, as will be described in fuller detail below, in contrast to "passive" measurement which uses only existing signals for detection.

As stated above, a system or method according to the invention is capable of working in conjunction with and enhancing EEG-based detection and prediction schemes (such as those described in Fischell et al. and Gotman, above). Preferably, the scheme is implemented in an intracranially implanted neurostimulator of the type generally described in Fischell et al., U.S. Pat. No. 6,016,449.

In one embodiment, active sensing of neural electrophysiological parameters can be used as an alternative detection or seizure prediction method, capable of being selectively activated during the physician's programming process, to be used instead of (or in conjunction with) other detection or prediction methods. In one embodiment of the invention, the various detection methods the device is capable of are selectively enabled based on the time of day.

Alternatively, the measured neural electrophysiological parameters can be used as weighting factors to alter the interpretation of EEG signals. In this scheme, EEG-based detection and electrophysiological measurements are used together to derive an aggregate likelihood of seizure activity.

In yet another embodiment, it is also possible to use the electrophysiological parameters as determined by a system or method according to the invention to drive device mode-switches. For example, when excitability or refractoriness is outside a range determined to be normal, certain other detection methods might be invoked that otherwise would not be performed. This would enable certain computationally intensive EEG analysis methods to be performed only when the patient's brain electrophysiology suggests an abnormal susceptibility to seizure activity, thereby enhancing battery life. Without this capability, it would be prohibitively power consuming to perform such complex analysis at all times.

If the inventive method determines that the likelihood of a seizure has increased, various actions may be taken to alert the patient or head off the seizure. For example, an alarm may be provided to the patient, advising the patient to cease certain activities or take medication, or electrical stimulation or automatic drug delivery may be administered. Continued monitoring of the electrophysiological parameters may be used to adjust the actions taken in a closed loop fashion, to drive the brain state away from the likelihood of developing a seizure.

As will be discussed in further detail below, the invention preferably measures the neural electrophysiological responsiveness of structures and functional pathways in the limbic system, although those skilled in the art will recognize that the measurement of parameters representative of electrophysiological responsiveness in other areas of the brain and in other manners may also be used to advantage in the detection of epileptic seizures (or other neurological disorders) according to the invention.

Specifically, it has been found that measurement of neural electrophysiological parameters according to the invention can be accomplished by inserting deep brain electrodes into a patient's hippocampus and parahippocampal gyrus (PHG). Periodically, an electrical stimulation signal is applied to the PHG electrode, and the evoked response in measured in the hippocampus via a signal received by the hippocampus electrode.

Preferably, a sequence of signals of various amplitudes is used to determine the excitability threshold. Similarly, a sequence of two-pulse waveforms with variable inter-pulse delays is used to determine the inhibitory strength. See, e.g., C. L. Wilson, "Neurophysiology of Epileptic Limbic Pathways in Intact Human Temporal Lobe," in P. Kotagal et al., ed., *The Epilepsies: Etiologies and Prevention*, San Diego: Academic Press 1999, 171–9.

The excitability and inhibitory strength parameters determined thereby are then processed and considered in light of baseline values and any trends that may develop.

It should be noted, of course, that while stimulation of the parahippocampal gyrus and measurement of the evoked response in the hippocampus may provide useful information in the described embodiment of the invention, the scheme described herein is also deemed to address the stimulation and detection in other brain structures, as well.

An apparatus according to the invention, in one embodiment, would include a control module, at least one brain lead with an electrode, and functionality responsive to the detection of at least one neural electrophysiological parameter.

The intracranially implanted control module would contain a battery and any electronics required to perform the detection, measurement, and treatment schemes enabled by the invention. The brain electrode would be adapted to sense and stimulate in at least two different locations in the patient's brain. The electronics in the control module would be configured to provide electrical stimulation via the brain lead and electrode to a first location in the patient's brain; any evoked response in a second location in the patient's brain is received by the brain electrode and transmitted to the electronics via the lead.

The electronics would be further adapted to selectively perform a method of measuring the neural electrophysiological parameters of excitability and refractoriness (inhibition), as described below, and performing an action in response to the measured parameters or a trend in the measured parameters.

An embodiment of the method of the invention for sensing excitability (as performed by the electronics in an apparatus according to the invention) would be carried out by providing a stimulation pulse of low amplitude to a first location of the patient's brain, receiving a response signal from a second location of the patient's brain, and processing the response signal to determine whether it is representative of a fully developed evoked response. If the response signal is not representative of an evoked response, the method continues by increasing the amplitude of the stimulation pulse and repeating the providing, receiving, and processing steps. When the response signal represents a fully developed evoked response, the amplitude of the stimulation pulse is deemed to exceed the excitability threshold. Note that the "threshold" may be statistical in nature, and more than one determination of the threshold may be used to generate a statistical representation of the threshold.

An embodiment of the method of the invention for sensing refractoriness (as performed by the electronics in an apparatus according to the invention) would be carried out by providing a pair of stimulation pulses (each having an amplitude greater than the excitability threshold) separated by a short delay to a first location of the patient's brain, receiving a response signal from a second location of the patient's brain, and processing the response signal to determine whether it represents a single evoked response or a pair of evoked responses. If the response signal represents a single evoked response (the second one having been inhibited), the method continues by lengthening the delay and repeating the providing, receiving, and processing steps. When the response signal represents a pair of evoked responses (the second response being distinct from the first stimulus), the delay between the stimulation pulses is deemed to exceed the refractory period (at the stimulation amplitude selected) of the pathway between the stimulating and detecting electrodes. Note that the "refractory period" may be statistical in nature, and more than one determination of the refractory period may be used to generate a statistical representation of that parameter.

It is anticipated that averaging of responses from stimulation pulses occurring at fixed amplitudes or delays can provide better discrimination of evoked responses.

The invention is directed generally to a diagnostic technique for determining neural electrophysiological parameters. Although a device capable of performing the invention may also be capable of delivering therapeutic stimulation, it should be noted that the stimulation pulses used to measure the electrophysiological parameters, such as excitability and refractoriness, is not therapeutic in nature. As a general proposition, the stimulation delivered by the invention is intended not to disrupt normal neurological patterns, but to give insight into brain's susceptibility to seizure activity. This is accomplished through the measurement and analysis of evoked responses. The system and method of the invention has several advantages over alternative known approaches for predicting and detecting ictal activity. In particular, it is believed that an apparatus or method implementing the invention would provide increased accuracy, an earlier indication of approaching ictal activity, and reduced computational requirements in comparison to alternative approaches.

With regard to increased accuracy, it is contemplated that the invention facilitates detection with fewer false positives and false negatives than alternative approaches.

With regard to earlier indications of ictal activity, it is believed that a system or method according to the invention would be able to detect abnormal electrophysiological parameters in advance of any detectable anomaly in EEG signals, thereby providing greater advance warning of a potential seizure.

With regard to reduced computational requirements, it is understood that the neural electrophysiological parameters the invention is adapted to measure can be used to select or de-select different operating modes of an implantable device, invoking the most complex detection and measurement schemes only when the electrophysiological parameters warrant it.

BRIEF DESCRIPTION OF THE DRAWINGS

These and other objects, features, and advantages of the invention will become apparent from the detailed description below and the accompanying drawings, in which.

DETAILED DESCRIPTION OF THE INVENTION

The invention is described below, with reference to detailed illustrative embodiments. It will be apparent that a system according to the invention may be embodied in a wide variety of forms. Consequently, the specific structural and functional details disclosed herein are representative and do not limit the scope of the invention.

Figure 1:
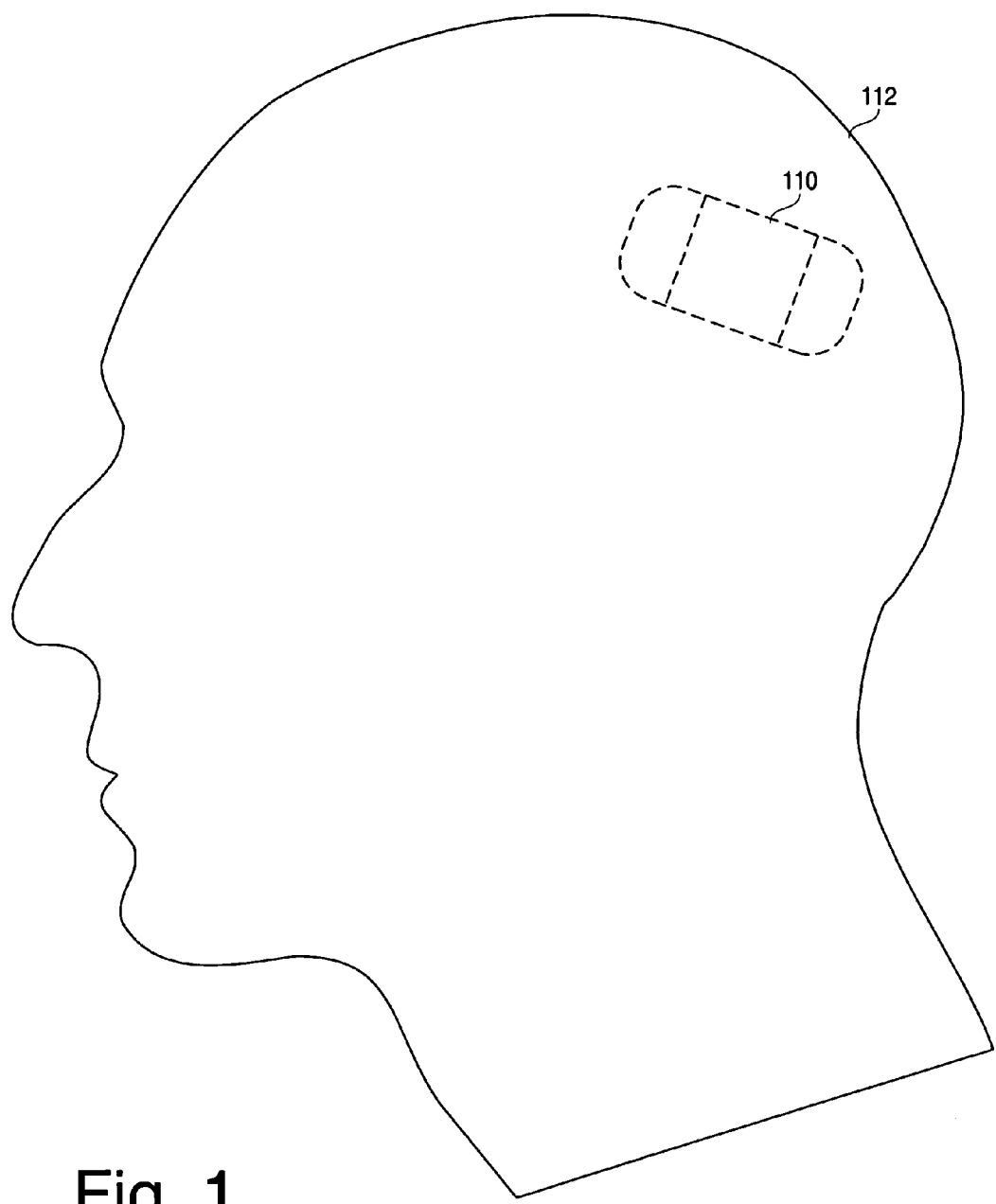
FIG. 1 is a schematic illustration of a patient's head showing the placement of an implantable neurostimulator according to an embodiment of the invention.

FIG. 1 depicts an intracranially implanted device 110 according to the invention, which in one embodiment is a small self-contained responsive neurostimulator. As the term is used herein, a responsive neurostimulator is a device capable of detecting ictal activity (or other neurological events) and providing therapy (often electrical stimulation) in response to that activity, where the therapy is specifically intended to terminate the ictal activity, treat a neurological event, or prevent an unwanted neurological event from occurring.

Figure 2:
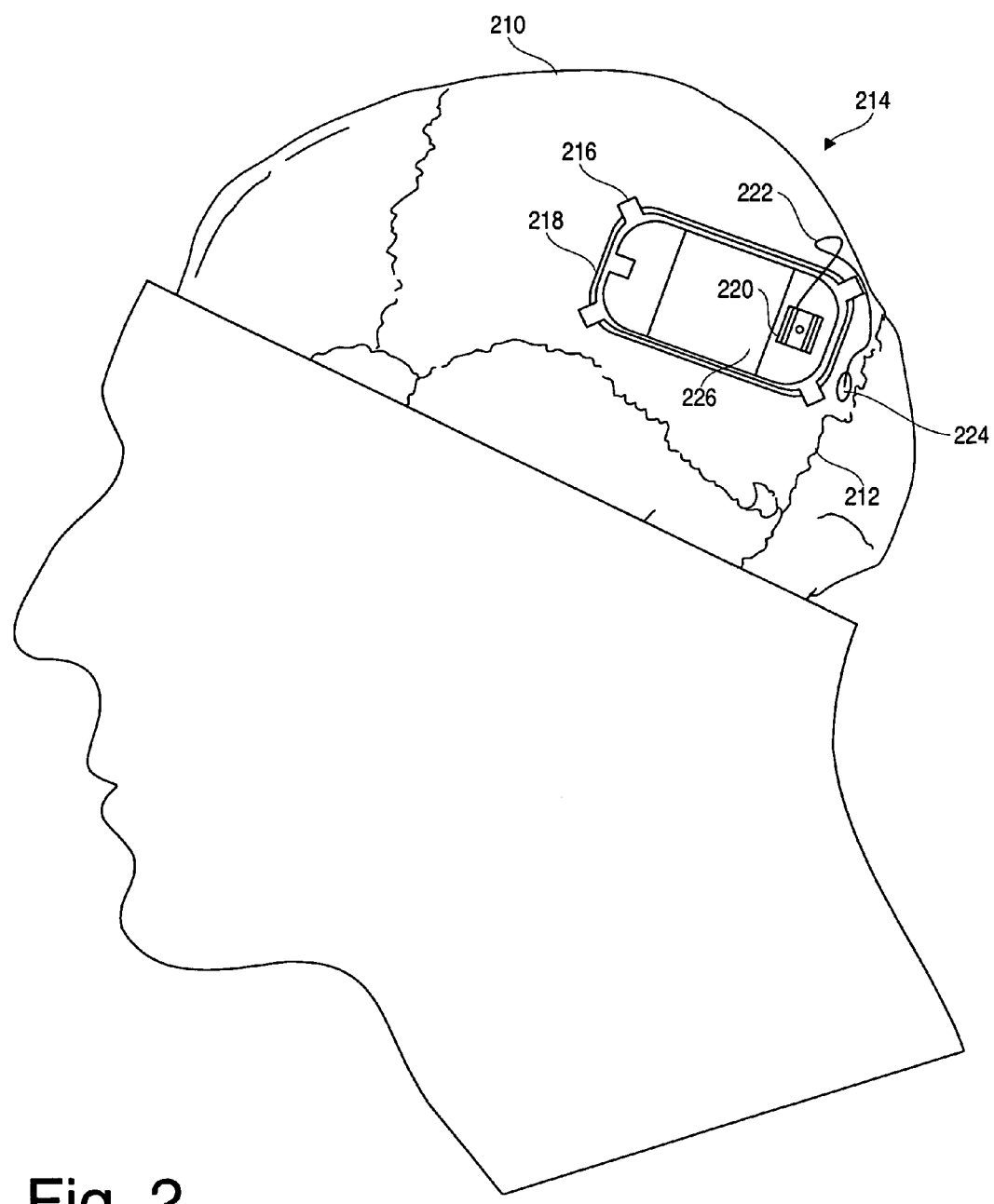
FIG. 2 is a schematic illustration of a patient's cranium showing the implantable neurostimulator of FIG. 1 as implanted, including leads extending to the patient's brain.

In the disclosed embodiment, the neurostimulator is implanted intracranially in a patient's parietal bone 210, in a location anterior to the lambdoidal suture 212 (see FIG. 2). It should be noted, however, that the placement described and illustrated herein is merely exemplary, and other locations and configurations are also possible, in the cranium or elsewhere, depending on the size and shape of the device and individual patient needs, among other factors. The device 110 is preferably configured to fit the contours of the patient's cranium 214. In an alternative embodiment, the device 110 is implanted under the patient's scalp 112 but external to the cranium; it is expected, however, that this configuration would generally cause an undesirable protrusion in the patient's scalp where the device is located. In yet another alternative embodiment, when it is not possible to implant the device intracranially, it may be implanted pectorally (not shown), with leads extending through the patient's neck and between the patient's cranium and scalp, as necessary.

It should be recognized that the embodiment of the device 110 described and illustrated herein is preferably a responsive neurostimulator for detecting and treating epilepsy by detecting seizure precursors and preventing and/or terminating epileptic seizures. However, a primary function of a device according to the invention is to detect any increased likelihood of the brain developing a seizure by identifying trends and conditions suggesting that increased likelihood, taking actions to prevent the seizure from occurring or terminate the seizure once it has begun, and using neurological conditions (including electrophysiological measurements) to specify or adjust the actions taken.

In an alternative embodiment of the invention, the device 110 is not a responsive neurostimulator, but is an apparatus capable of detecting neurological conditions and events and performing actions in response thereto. The actions performed by such an embodiment of the device 110 need not be therapeutic, but may involve data recording or transmission, providing warnings to the patient, or any of a number of known alternative actions. Such a device will typically act as a diagnostic device when interfaced with external equipment, as will be discussed in further detail below.

The device 110, as implanted intracranially, is illustrated in greater detail in FIG. 2. The device 110 is affixed in the patient's cranium 214 by way of a ferrule 216. The ferrule 216 is a structural member adapted to fit into a cranial opening, attach to the cranium 214, and retain the device 110.

To implant the device 110, a craniotomy is performed in the parietal bone anterior to the lambdoidal suture 212 to define an opening 218 slightly larger than the device 110. The ferrule 216 is inserted into the opening 218 and affixed to the cranium 214, ensuring a tight and secure fit. The device 110 is then inserted into and affixed to the ferrule 216.

As shown in FIG. 2, the device 110 includes a lead connector 220 adapted to receive one or more electrical leads, such as a first lead 222. The lead connector 220 acts to physically secure the lead 222 to the device 110, and facilitates electrical connection between a conductor in the lead 222 coupling an electrode to circuitry within the device 110. The lead connector 220 accomplishes this in a substantially fluid-tight environment with biocompatible materials.

The lead 222, as illustrated, and other leads for use in a system or method according to the invention, is a flexible elongated member having one or more conductors. As shown, the lead 222 is coupled to the device 110 via the lead connector 220, and is generally situated on the outer surface of the cranium 214 (and under the patient's scalp 112), extending between the device 110 and a burr hole 224 or other cranial opening, where the lead 222 enters the cranium 214 and is coupled to a depth electrode (see FIG. 4) implanted in a desired location in the patient's brain. If the length of the lead 222 is substantially greater than the distance between the device 110 and the burr hole 224, any excess may be urged into a coil configuration under the scalp 112. As described in U.S. Pat. No. 6,006,124 to Fischell, et al., which is hereby incorporated by reference as though set forth in full herein, the burr hole 224 is sealed after implantation to prevent further movement of the lead 222; in an embodiment of the invention, a burr hole cover apparatus is affixed to the cranium 214 at least partially within the burr hole 224 to provide this functionality.

The device 110 includes a durable outer housing 226 fabricated from a biocompatible material. Titanium, which is light, extremely strong, and biocompatible, is used in analogous devices, such as cardiac pacemakers, and would serve advantageously in this context. As the device 110 is self-contained, the housing 226 encloses a battery and any electronic circuitry necessary or desirable to provide the functionality described herein, as well as any other features. As will be described in further detail below, a telemetry coil may be provided outside of the housing 226 (and potentially integrated with the lead connector 220) to facilitate communication between the device 110 and external devices.

The neurostimulator configuration described herein and illustrated in FIG. 2 provides several advantages over alternative designs. First, the self-contained nature of the neurostimulator substantially decreases the need for access to the device 110, allowing the patient to participate in normal life activities. Its small size and intracranial placement causes a minimum of cosmetic disfigurement. The device 110 will fit in an opening in the patient's cranium, under the patient's scalp, with little noticeable protrusion or bulge. The ferrule 216 used for implantation allows the craniotomy to be performed and fit verified without the possibility of damaging the device 110, and also provides protection against the device 110 being pushed into the brain under external pressure or impact. A further advantage is that the ferrule 216 receives any cranial bone growth, so at explant, the device 110 can be replaced without removing any bone screws—only the fasteners retaining the device 110 in the ferrule 216 need be manipulated.

Figure 3:
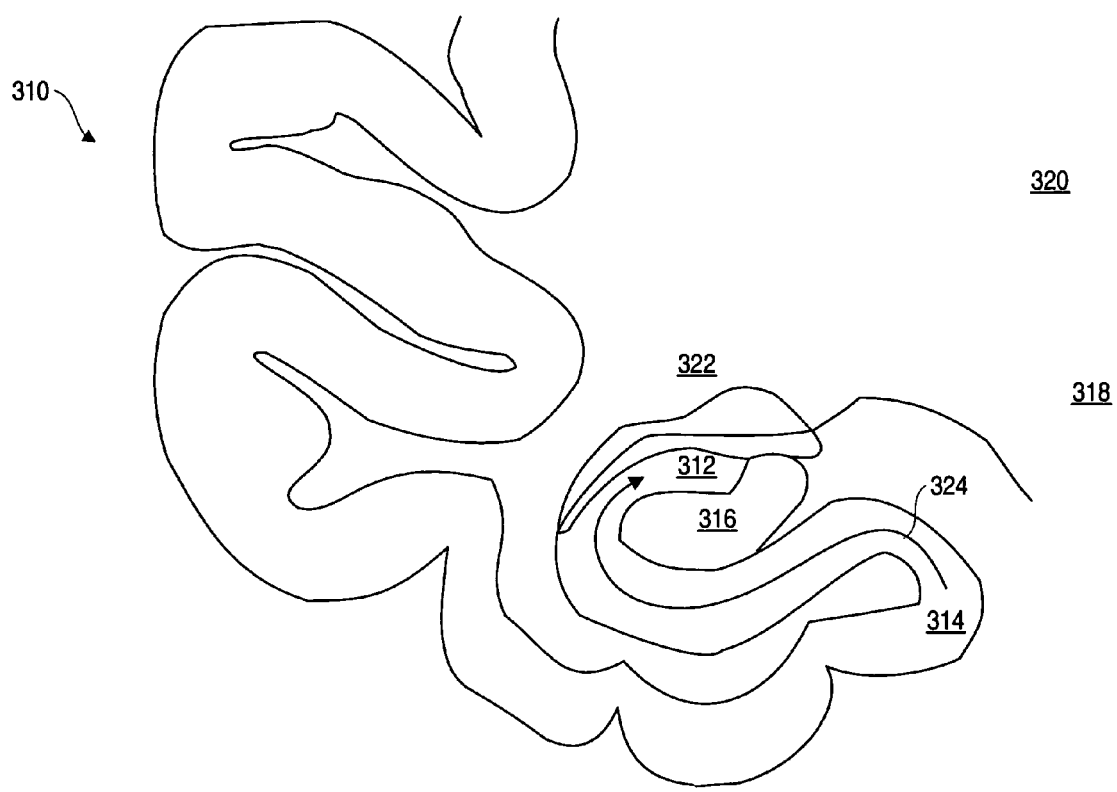
FIG. 3 is a schematic illustration of several regions of a patient's brain, including the hippocampus and parahippocampal gyrus.

As set forth above, the invention is directed to the measurement of the patient's susceptibility to undesired neurological events through the analysis of brain electrophysiology, including excitability and refractoriness. An exemplary coronal section of a human brain 310 is shown in FIG. 3, which primarily shows a temporal lobe. As briefly explained above, and as described in further detail below, the limbic system is implicated in some cases of epilepsy. The normal human limbic system is responsible for processing and regulating emotions, feelings, and moods.

Several structures of the limbic system are visible in the brain section 310 of FIG. 3. The hippocampus 312 is a structure believed to be involved in memory and learning in humans. The parahippocampal gyrus 314, which is also believed to be involved in long-term memory processes, is an external portion of the temporal lobe. The dentate gyrus 316 is located between the hippocampus 312 and the parahippocampal gyrus 314. The hypothalamus 318 and thalamus 320 are portions of the brain located deep within the temporal lobe near the plane separating the two lateral hemispheres. The amygdala 322 is located near the hippocampus 312.

Many of these structures of the limbic system, as well as the functional pathways involved in communication among these structures, are often implicated in epilepsy. For example, the Wilson article (referenced above) suggests that a perforant pathway (indicated by a representative arrow 324 that is not meant to indicate the actual path of neuronal communication) between the entorhinal cortex (of which the parahippocampal gyrus 314 forms a part) and the anterior portion of the hippocampus 312 is subject to hypersynchronous neuronal activity in a substantial number of epilepsy sufferers.

Accordingly, in this subpopulation of epilepsy sufferers and others, it will be advantageous to measure various electrophysiological parameters in the pathway connecting the parahippocampal gyrus 314 and the hippocampus.

The coronal brain section 310 of FIG. 3 represents a functional illustration of several structures of the limbic system. As can be appreciated, there is a complex interrelationship among the illustrated structures (in particular the hippocampus 312 and the parahippocampal gyrus 314) and many of the other structures of the limbic system; it should be noted that the gross generalization of the limbic system pathways presented herein is not a complete description of the functionality of the brain, the limbic system, or any portion thereof. It is intended to be illustrative of diagnosis, measurement, detection, and treatment options facilitated by the invention.

For example, as described in the Wilson article (referenced above), an interrelationship is described among the hippocampus (including its anterior, middle, and posterior portions), the presubicular cortex, the entorhinal cortex, the parahippocampal gyrus (especially the middle and posterior portions thereof), and the amygdala. There are also believed to be various pathways implicating many other brain structures, including but not limited to the dentate gyrus 316, the hypothalamus 318, the thalamus 320, the retrosplenial cortex, the paleocortex, the neocortex, the septal area, and the cingulated gyrus.

It is understood that the detection and measurement techniques of the present invention may be advantageously employed in connection with any or all of these pathways, as well as others, either between functionally distinct brain structures or within a single brain structure. For example, hippocampal sclerosis (particularly found in the anterior hippocampus) is associated with epilepsy, which in turn may affect (or be affected by) the electrophysiological characteristics of the associated pathways, so measurement and detection according to the invention would be advantageous in detecting and treating such deterioration.

Figure 4:
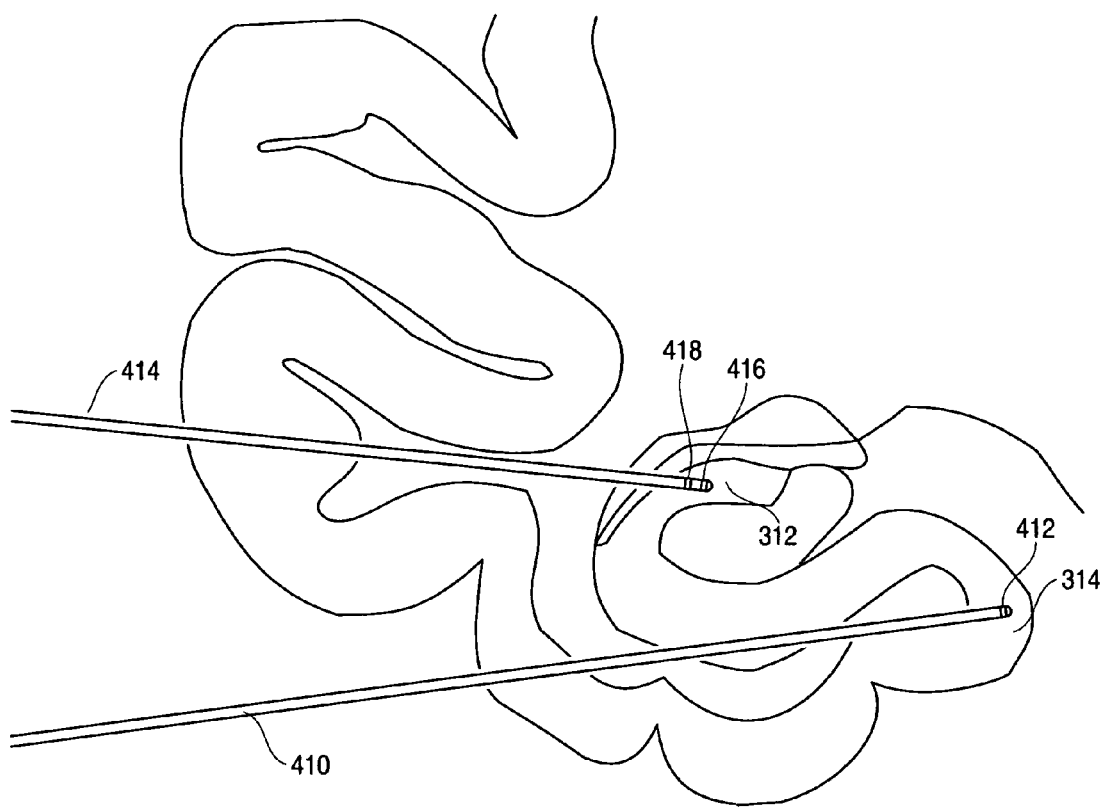
FIG. 4 is a schematic sectional view of a patient's brain illustrating the placement of electrodes in the regions illustrated in FIG. 3 in one embodiment of the invention.

An electrode configuration capable of accomplishing this in conjunction with the invention is illustrated in FIG. 4.

In FIG. 4, a first depth lead 410 is implanted in the patient's parahippocampal gyrus (PHG) 314. The first depth lead 410, which is used to electrically stimulate the PHG 314, includes a first conductive electrode 412 placed in contact with brain tissue in the PHG 314; the remainder of the surface of the first depth lead is insulating. The first conductive electrode 412 is in communication with electronic circuitry in the device 110 by a conductor in the first depth lead 410. Similarly, a second depth lead 414 is implanted in the patient's hippocampus 312. The second depth lead 414, which is used to sense responses to stimulation provided by the first electrode 412, includes a second conductive electrode 416 and preferably a third conductive electrode 418 to facilitate bipolar sensing placed in contact with brain tissue in the hippocampus 312. As with the first depth lead 410, the remainder of the second depth lead 414 is insulating, but internal conductors connect the device 110 to the second and third conductive electrodes 416 and 418.

In the disclosed embodiment, the depth leads 410 and 414 are primarily fabricated from a durable biocompatible insulating material, such as a silicone elastomer. The conductive electrodes 412, 416, and 418 may be a platinum/iridium alloy, pure platinum, or iridium oxide, all of which are conductive biocompatible materials suitable for use as implanted electrodes.

In the illustrated embodiment, the first depth lead 410 has a single conductive electrode 412 and the second depth lead 414 has two conductive electrodes 416 and 418. However, it should be noted that it may be advantageous to have additional conductive electrodes at or near the distal end of each depth lead, each individually connected to the device 110 by a separate conductor in the corresponding lead (such as the lead 222). Such a configuration would provide multiple stimulation or sensing options in each region of the brain; it might also be possible to perform stimulation and sensing with a single depth lead, provided conductive electrodes are located appropriately along a single line of approach.

It should be noted that the surgical approaches for the depth leads 410 and 414 illustrated in FIG. 4 are shown for purposes of explanation only; it may not be possible in a particular patient (or any patient) to implant the electrodes as indicated. Other anatomical features and obstacles (such as vasculature) may be present and may force the use of alternatives. It should be noted that numerous alternative stereotactic surgical approaches to the brain structures described herein are certainly possible, and would be known to a neurologist or neurosurgeon of ordinary skill in the art.

As briefly described above in connection with FIG. 2, the depth leads are implanted by first forming an opening in the cranium, typically a burr hole (such as the burr hole 224 of FIG. 2). The depth leads are stereotactically inserted through a cannula (with the assistance of a stylet to provide additional rigidity). Once the distal end of the lead, specifically the conducting electrode, is placed in a desired location, the cannula is removed, the stylet is retracted, and the electrode stays in place within the neural tissue. Although there ordinarily should be little or no force acting to move the electrode away from its desired location, the lead would be postoperatively physically retained in its desired location by a retention apparatus affixed to (and generally covering) the burr hole.

As stated above, temporal lobe epilepsy is often characterized by hypersynchronous neuronal discharges originating in the temporal lobe. The hippocampus 312, PHG 314, and other structures of the limbic system (FIG. 3) may have a role in this; they also may have a role in normal long-term memory, emotions, feelings, and moods.

Figure 5:
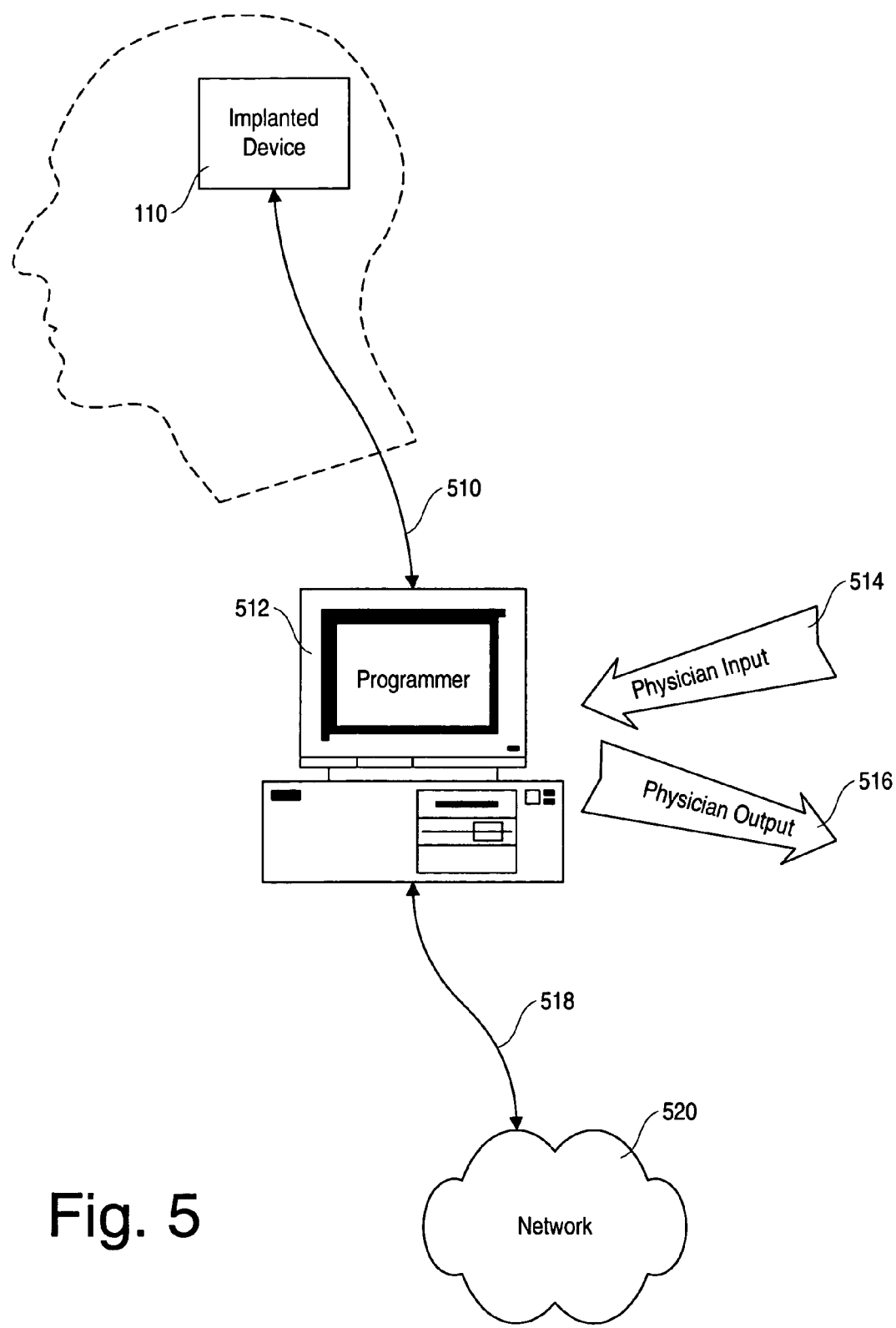
FIG. 5 is a block diagram illustrating context in which an implantable neurostimulator according to the invention is implanted and operated.

As stated above, and as illustrated in FIG. 5, a neurostimulator according to the invention operates in conjunction with external equipment. The device 110 is mostly autonomous (particularly when performing its usual measurement, detection, and stimulation capabilities), but preferably includes a selectable part-time wireless link 510 to external equipment such as a programmer 512. In the disclosed embodiment of the invention, the wireless link 510 is established by moving a wand (or other apparatus) having communication capabilities and coupled to the programmer 512 into range of the device 110. The programmer 512 can then be used to manually control the operation of the device 110, as well as to transmit information to or receive information from the device 110. Several specific capabilities and operations performed by the programmer 512 in conjunction with the device 110 will be described in further detail below, particularly with reference to FIGS. 6, 9–10, 12–13, and 15–17.

The programmer 512 is capable of performing a number of advantageous operations in connection with the invention. In particular, the programmer 512 is able to specify and set variable parameters in the device 110 to adapt the function of the device 110 to meet the patient's needs, download or receive data (including but not limited to stored EEG waveforms, parameters, or logs of actions taken) from the device 110 to the programmer 512, upload or transmit program code and other information from the programmer 512 to the device 110, or command the device 110 to perform specific actions or change modes as desired by a physician operating the programmer 512. To facilitate these functions, the programmer 512 is adapted to receive physician input 514 and provide physician output 516; data is transmitted between the programmer 512 and the device 110 over the wireless link 510.

The programmer 512 may be coupled via a communication link 518 to a network 520 such as the Internet. This allows any information downloaded from the device 110, as well as any program code or other information to be uploaded to the device 110, to be stored in a database at one or more data repository locations (which may include various servers and network-connected programmers like the programmer 512). This would allow a patient (and the patient's physician) to have access to important data, including past treatment information and software updates, essentially anywhere in the world that there is a programmer (like the programmer 512) and a network connection.

Figure 6:
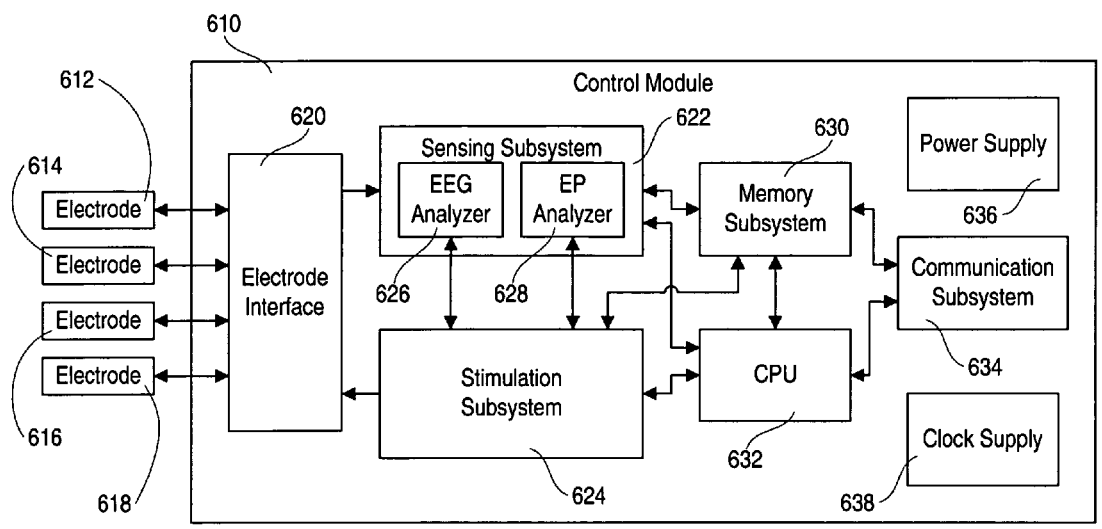
FIG. 6 is a block diagram illustrating the major subsystems of an implantable neurostimulator according to the invention.

An overall block diagram of the device 110 used for measurement, detection, and treatment according to the invention is illustrated in FIG. 6. Inside the housing 226 of the device 110 are several subsystems making up a control module 610. The control module 610 is capable of being coupled to a plurality of electrodes 612, 614, 616, and 618 (each of which may be connected to the control module 610 via a lead that is analogous or identical to the lead 222 of FIG. 2) for sensing and stimulation. In the illustrated embodiment, the coupling is accomplished through the lead connector 220 (FIG. 2). Although four electrodes are shown in FIG. 6, it should be recognized that any number is possible; in fact, it is possible to employ an embodiment of the invention that uses a single lead with at least two electrodes, or two leads each with a single electrode (or with a second electrode provided by a conductive exterior portion of the housing 226 in one embodiment), although bipolar sensing between two closely spaced electrodes on a lead is preferred to minimize common mode signals including noise.

The electrodes 612–618 are connected to an electrode interface 620. Preferably, the electrode interface is capable of selecting each electrode as required for sensing and stimulation; accordingly the electrode interface is coupled to a sensing subsystem 622 and a stimulation subsystem 624. The electrode interface is also may provide any other features, capabilities, or aspects, including but not limited to amplification, isolation, and charge-balancing functions, that are required for a proper interface with neurological tissue and not provided by any other subsystem of the device 110.

The sensing subsystem 622 includes an EEG analyzer function 626 and an electrophysiology (EP) analyzer function 628. The EEG analyzer function 626 is adapted to receive EEG signals from the electrodes 612–618, through the electrode interface 620, and to process those EEG signals to identify neurological activity indicative of a seizure or a precursor to a seizure. One way to implement such EEG analysis functionality is disclosed in detail in U.S. Pat. No. 6,016,449 to Fischell et al., incorporated by reference above. The EP analysis functionality of the invention is described in further detail below, particularly in connection with FIGS. 9–17. The sensing may optionally also contain further sensing and detection capabilities, including but not limited to parameters derived from other physiological conditions (such as temperature, ECG, blood pressure, etc.).

The stimulation subsystem 624 is capable of applying electrical stimulation to neurological tissue through the electrodes 612–618. This can be accomplished in any of a number of different manners. For example, it may be advantageous in some circumstances to provide stimulation in the form of a substantially continuous stream of pulses. Preferably, therapeutic stimulation is provided in response to abnormal events detected by the EEG analyzer function 626 of the sensing subsystem 622. As illustrated in FIG. 6, the stimulation subsystem 624 and the EEG analyzer function 626 are connected; this facilitates the ability of stimulation subsystem 624 to provide responsive stimulation as well as an ability of the sensing subsystem 622 to blank the amplifiers while stimulation is being performed to minimize stimulation artifacts. It is contemplated that the parameters of the stimulation signal (e.g., frequency, duration, waveform) provided by the stimulation subsystem 624 would be specified by other subsystems in the control module 610, as will be described in further detail below.

The EP analyzer function 628 is also in communication with the stimulation subsystem 624. As will be described below, the electrophysiological measurement capabilities of the invention are active and dependent upon analysis of responses to particular stimulation signals provided by the device 110; the link between the EP analyzer 628 and the stimulation subsystem 624 enables this functionality.

Also in the control module 610 is a memory subsystem 630 and a central processing unit (CPU) 632, which can take the form of a microcontroller. The memory subsystem is coupled to the sensing subsystem 622 (e.g., for receiving and storing data representative of sensed EEG signals and evoked responses), the stimulation subsystem 624 (e.g., for providing stimulation waveform parameters to the stimulation subsystem), and the CPU 632, which can control the operation of the memory subsystem 630. In addition to the memory subsystem 630, the CPU 632 is also connected to the sensing subsystem 622 and the stimulation subsystem 624 for direct control of those subsystems.

Also provided in the control module 610, and coupled to the memory subsystem 630 and the CPU 632, is a communication subsystem 634. The communication subsystem 634 enables communication between the device 110 (FIG. 1) and the outside world, particularly the external programmer 512 (FIG. 5). As set forth above, the disclosed embodiment of the communication subsystem 634 includes a telemetry coil (which may be situated outside of the housing 226) enabling transmission and reception of signals, to or from an external apparatus, via inductive coupling. Alternative embodiments of the communication subsystem 634 could use an antenna for an RF link or an audio transducer for an audio link.

Rounding out the subsystems in the control module 610 are a power supply 636 and a clock supply 638. The power supply 636 supplies the voltages and currents necessary for each of the other subsystems. The clock supply 638 supplies substantially all of the other subsystems with any clock and timing signals necessary for their operation.

It should be observed that while the memory subsystem 630 is illustrated in FIG. 6 as a separate functional subsystem, the other subsystems may also require various amounts of memory to perform the functions described above and others. Furthermore, while the control module 610 is preferably a single physical unit contained within a single physical enclosure, namely the housing 226 (FIG. 2), it may comprise a plurality of spatially separate units each performing a subset of the capabilities described above. Also, it should be noted that the various functions and capabilities of the subsystems described above may be performed by electronic hardware, computer software (or firmware), or a combination thereof. The division of work between the CPU 632 and the other functional subsystems may also vary—the functional distinctions illustrated in FIG. 6 may not reflect the integration of functions in a real-world system or method according to the invention.

Figure 7:
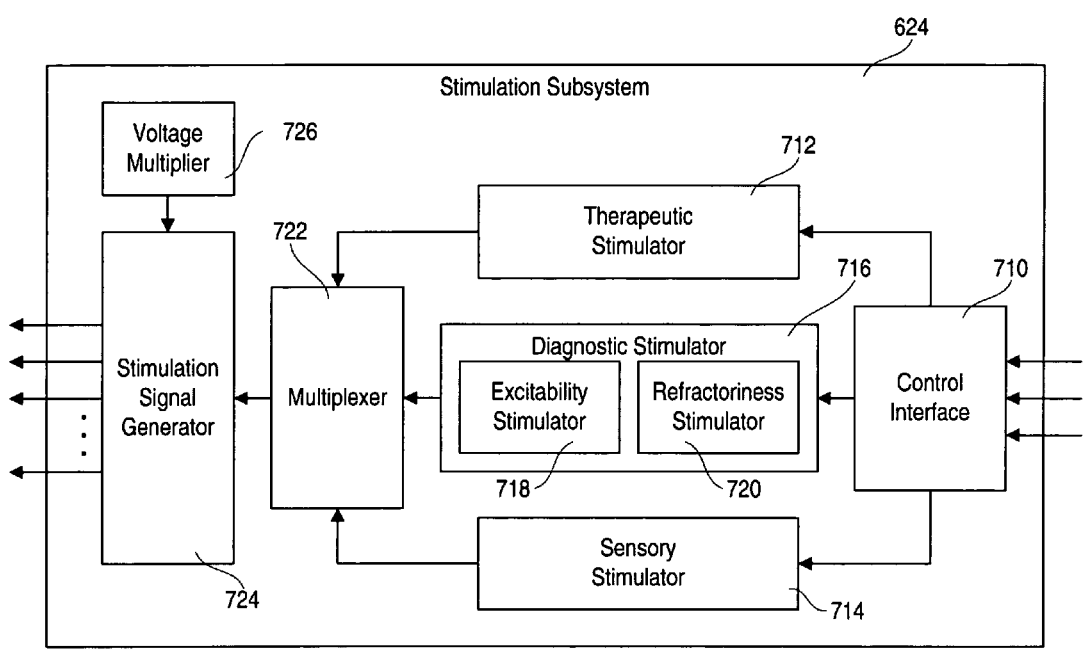
FIG. 7 is a block diagram illustrating the components of the stimulation subsystem of the implantable neurostimulator shown in FIG. 6.

The various functions and capabilities of the stimulation subsystem 624 are illustrated in greater detail in FIG. 7. Consistent with FIG. 6, inputs to the stimulation subsystem 624 are shown on the right, and outputs are on the left.

Referring initially to the input side of FIG. 6, the stimulation subsystem 624 includes a control interface 710, which receives commands, data, and other information from the CPU 632, the memory subsystem 630, and the sensing subsystem 622. The control interface 710 uses the received commands, data, and other information to control a therapeutic stimulator 712, a sensory stimulator 714, and a diagnostic stimulator 716. The therapeutic stimulator 712 is adapted to provide electrical stimulation signals appropriate for application to neurological tissue to terminate a present or predicted undesired neurological event, especially an epileptic seizure (or its precursor). As set forth above, the therapeutic stimulator 712 is typically activated in response to conditions detected by the sensing subsystem 622, but may also provide some substantially continuous stimulation. The sensory stimulator 714 is also typically activated in response to a detection by the sensing subsystem; it may electrically stimulate enervated tissue (such as the scalp) to provide a tactile sensation to the patient, or may alternatively include an audio or visual transducer to provide audiovisual cues (such as warnings) to the patient.

The diagnostic stimulator 716 includes two sub-functions, an excitability stimulator 718 and a refractoriness stimulator 720, though both functions may be performed by the same circuit under differing controls from the control interface 710. The excitability stimulator 718 and the refractoriness stimulator 720 both act under the control of the sensing subsystem 622 to provide the stimulation signals necessary for the effective measurement of electrophysiological parameters according to the invention. In the disclosed embodiment, the excitability stimulator 718 provides pulses at varying current levels to test the excitability of neural tissue (see FIGS. 9–11, described below), while the refractoriness stimulator 720 provides pairs of pulses with varying inter-pulse intervals to test the inhibitory characteristics of neural tissue (see FIGS. 12–14, described below).

The therapeutic stimulator 712, the sensory stimulator 714, and the diagnostic stimulator 716 are all coupled to a multiplexer 722, which is controllable to select the appropriate types of stimulation and pass them along to a stimulation signal generator 724. The multiplexer 722 may allow only one type of stimulation to be performed at a time, but in a presently preferred embodiment, the multiplexer 722 allows different types of stimulation to be selectively applied to the different electrodes 612–618, either sequentially or substantially simultaneously. The stimulation signal generator 724 receives commands and data from the therapeutic stimulator 712, the sensory stimulator 714, and the diagnostic stimulator 716, and generates electrical stimulation signals having the desired characteristics that are properly time-correlated and associated with the correct electrodes, and receives power from a controllable voltage multiplier 726 to facilitate the application of a proper voltage and current to the desired neurological tissue. The voltage multiplier 726 is capable of creating relatively high voltages from a battery power source, which typically has a very low voltage; circuits to accomplish this function are well known in the art of electronics design. The stimulation signal generator 724 has a plurality of outputs 728, which in the disclosed embodiment are coupled to the electrode interface 620 (FIG. 6). In various embodiments of the invention, the stimulation signal generator 724 can perform signal isolation, multiplexing, and queuing functions if the electrode interface 620 does not perform such functions.

It should be recognized that while various functional blocks are illustrated in FIG. 7, not all of them might be present in an operative embodiment of the invention. Furthermore, as with the overall block diagram of FIG. 6, the functional distinctions illustrated in FIG. 7, which are presented as separate functions for clarity and understandability herein, might not be meaningful distinctions in an implementation of the invention. For example, in the presently preferred embodiment, the various stimulation types (provided in FIG. 7 by stimulators 712–716) are all accomplished with a single circuit selectively controlled with different parameters; there is a single controllable stimulator capable of selectively providing signals for therapeutic stimulation, diagnostic stimulation, and sensory stimulation.

Figure 8:
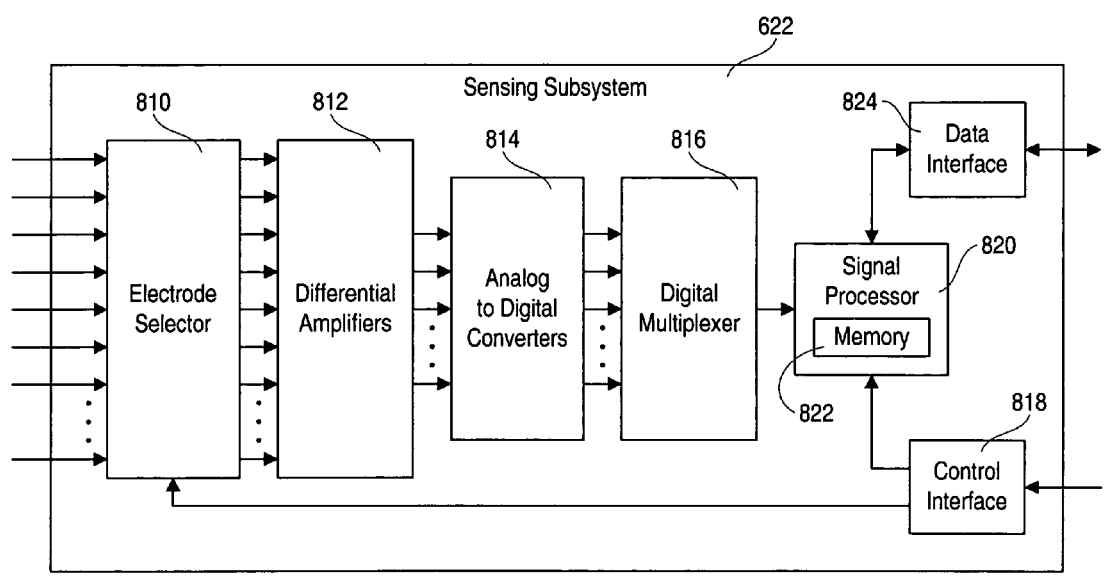
FIG. 8 is a block diagram illustrating the components of the measurement subsystem of the implantable neurostimulator shown in FIG. 6.

FIG. 8 illustrates details of the sensing subsystem 622 (FIG. 6). Inputs from the electrodes 612–618 are on the left, and connections to other subsystems are on the right.

Signals received from the electrodes 612–618 (as routed through the electrode interface 620) are received in an electrode selector 810. The electrode selector 810 allows the device to select which electrodes (of the electrodes 612–618) should be routed to which individual channels of the sensing subsystem 622, based on control received through a control interface 818 from the memory subsystem 630 or the CPU 632 (FIG. 6). The electrode selector 810 provides signals corresponding to each selected electrode (of the electrodes 612–618) to a bank of differential amplifiers 812, which are gain-matched and adapted to amplify the input signals to a level capable of being processed by a system or method according to the invention. The bank of differential amplifiers 812 includes a plurality of channels; each channel receives a pair of electrode signals from the electrode selector 810 and amplifies the difference in potential between them to derive an analog input signal representative of the bipolar signal between two selected electrodes.

The bank of amplifiers 812 transmits the amplified analog input signals to a bank of analog-to-digital converters (ADCs) 814, which generates a number of digital signals corresponding to the analog input signals. These digital signals are passed to a multiplexer 816, which interleaves the digital signals. The multiplexed input signal is then fed from the multiplexer 816 to a signal processor 820.

Although FIG. 8 illustrates the multiplexer 816 placed between the bank of ADCs 814 and the signal processor 820, it should be noted that a multiplexing function can be performed between the electrode selector 810 and the bank of differential amplifiers 812 (which, in this embodiment, would be a single amplifier), or between the differential amplifiers 812 and the ADCs 814 (in this embodiment, a single ADC). There are tradeoffs inherent in any of these configurations that would be known to a practitioner of ordinary skill in the arts of electronics design and signal processing. For example, placement of the multiplexer 816 before the ADC 814 would enable the use of a single ADC for multiple input channels, but requires a high speed ADC that may require more current to operate. This can be avoided by locating the multiplexer 816 after a bank of ADCs, as suggested above, but one low power ADC would then be required for each input channel.

The signal processor 820 is preferably a special-purpose digital signal processor (DSP) adapted for use with the invention, or in an alternative embodiment, may comprise a programmable general-purpose DSP. In the disclosed embodiment, the signal processor has its own scratchpad memory area 822 used for local storage of data and program variables when the signal processing is being performed. In either case, the signal processor performs the measurement and detection methods set forth in FIGS. 9–17, described below. Any results from such methods, as well as any digitized signals intended for storage transmission to external equipment, are passed to various other subsystems of the control module 610, including the memory subsystem 630 and the CPU 632 (FIG. 6) through a data interface 824.

Figure 9:
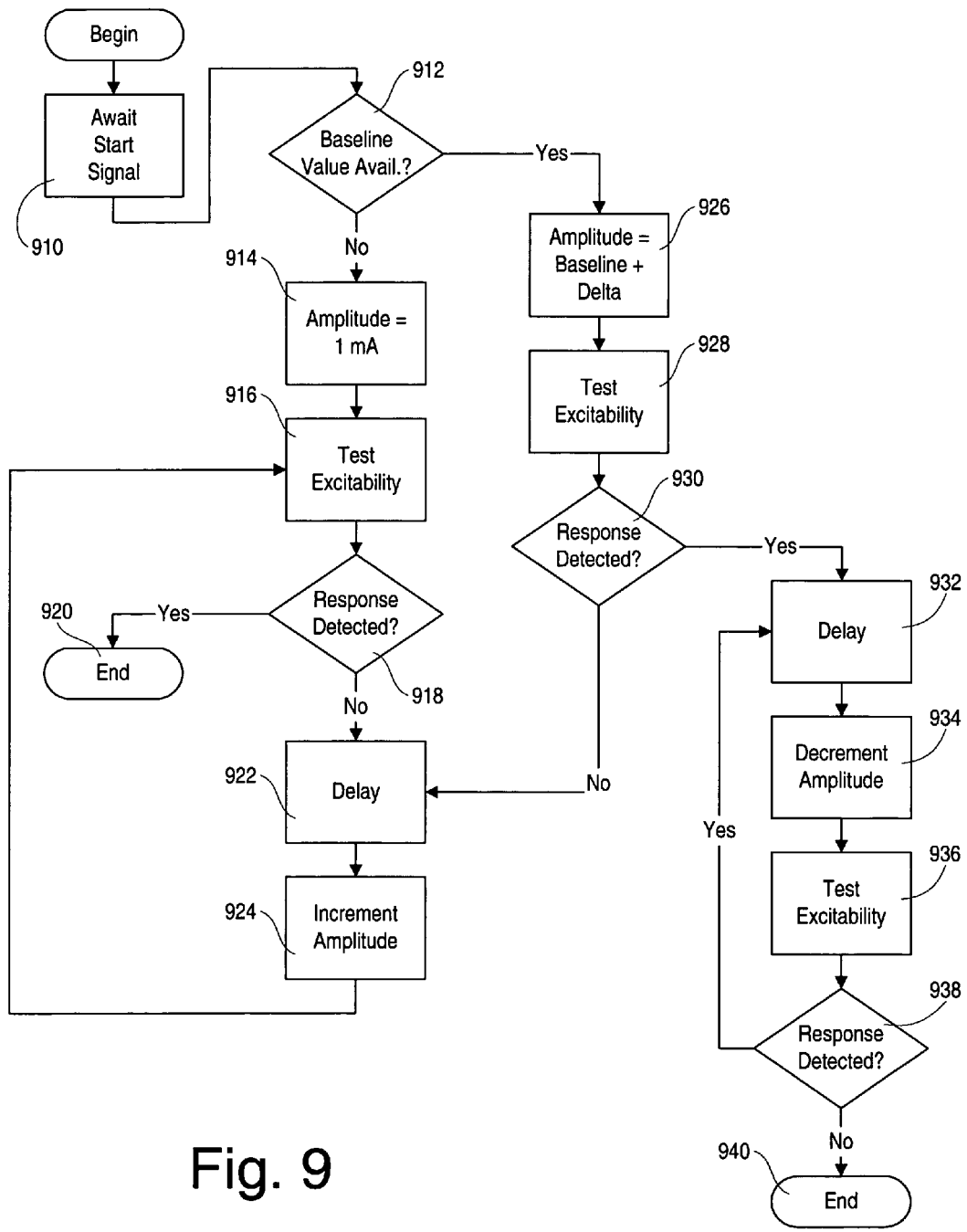
FIG. 9 is a flow chart illustrating the process performed in measuring the excitability of a region of a patient's brain in an embodiment of the invention.

The method of measuring excitability of neural tissue as performed by the EP analyzer 628 of the sensing subsystem 622 (in connection with the stimulation subsystem 624) is illustrated in the form of a flow chart in FIG. 9. At the outset, it should be noted that the device 110 (FIG. 1), as well as its constituent components, is capable of performing numerous tasks in a substantially simultaneous manner. The measurement of electrophysiological parameters according to the invention is preferably not performed continuously, so until a measurement of excitability is called for (either on a scheduled, commanded, or responsive basis), the method of measuring excitability begins by awaiting a start signal (step 910).

Once a start signal has been received, indicating that a measurement of excitability is desired, the memory subsystem 630 is queried for the existence of a baseline, or expected, excitability value (step 912). The baseline excitability value, if one exists, can be selected from previously measured values, preferably at a comparable time of day (or with the patient in a comparable state of alertness), or from a programmed selected value, which also may be time-dependent. In the disclosed embodiment, the baseline excitability value is stored in the memory subsystem 630 by the external programmer 512. Prior to programming the device 110, the patient's physician commands the device 110 (via the programmer 512) to perform a sequence of excitability measurements by the methods set forth below; the resulting waveforms, rather than being automatically analyzed by the device, are downloaded to the programmer 512 for consideration by the physician. The physician can then select the results most representative of an excitatory response, and program the parameters of that response into the device for future automatic use as a baseline threshold value. This procedure can be performed several times, at various times of day, to give the physician multiple options in choosing appropriate parameters, and to account for diurnal cyclical variation in excitability, as described below.

It should be noted that in some patients, it is also possible to establish baseline values by comparing measured excitability values in the epileptogenic region of the patient's brain to measurements taken in analogous structures in the patient's non-epileptogenic hemisphere. However, this approach would require further computation (and approximately twice the number of measurements) and the implantation of electrodes in the patient's healthy brain structure, which might not be desirable in some circumstances, and might not be possible in some patients with abnormal neurophysiology in both hemispheres.

If a baseline value is not present or is no longer considered valid, an excitability value must be computed without the benefit of any expected value, which the new value would likely be in the vicinity of. In the simplified method set forth in FIG. 9, a linear search is performed for the excitability value. The search begins by setting an initial pulse amplitude (in current) to, for example, 1 mA (step 914). This is a lower bound value that is not expected to trigger neural excitation as determined by the physician by commanding the test manually. The neural tissue excitability is then tested at the pulse amplitude (step 916) by applying an electrical stimulating pulse to an electrode implanted at a stimulation site and measuring the response in another electrode implanted at a measurement site (see FIG. 4).

Excitability is verified by measuring the peak amplitude of any responsive signal received by the electrode implanted at the measurement site. If there is an excitatory response, there will be a significant waveform amplitude of the measured response signal (especially if a number of trials are averaged, where such number is preferably two to four) in comparison to measurements taken below the excitability threshold. Alternatively, the response signal can be assigned a threshold as a percentage of the stimulation amplitude, or as a static programmed value. The threshold for verifying that a response occurred may either be set as fixed value determined by commanding the test under physician control, or by setting an adaptive threshold above the averaged baselined EEG signal. Further techniques for identifying evoked responses will be described below.

If a response is detected (step 918), the neural tissue being measured is excitable at the amplitude being tested, and the process of searching for an excitability threshold is finished (step 920). Otherwise, a delay (which can typically range from 15 seconds to 30 minutes) is taken to allow the neural tissue to recover from any effects of the most recent excitability test pulse (step 922), and to allow any inhibitory response to diminish, the amplitude is incremented by 1 mA (step 924), or some other user selectable increment, and the method repeats by testing excitability again at the new amplitude (step 916). It is contemplated that a bounds checking step would be advantageous; once the amplitude reaches a predetermined upper level, the method should be terminated even if excitability has not been detected. Moreover, while steps 914 and 924 above indicate that amplitude should start at 1 mA and be incremented in steps of 1 mA, those numbers are for purposes of illustration only and any sufficiently low starting amplitude and suitable step size, uniform or not, would be appropriate.

If a baseline value is available (step 912) when the method begins, there is no need to test the entire range of amplitudes. Rather, the initial amplitude is set to the expected baseline value plus a delta (step 926), wherein the delta is half of the smallest acceptable resolution interval. The excitability is then tested at the initial amplitude (step 928). If a response is not detected (step 930), then the initial amplitude is below the excitability threshold, and after a delay (step 922), the amplitude is incremented (step 924) and another measurement is taken. On the other hand, if a response is detected (step 930), the initial amplitude is above the excitability threshold, so after a delay (step 932) the amplitude is decremented (step 934) and excitability is tested again (step 936). The method continues by delaying (step 932) and decrementing (step 934) if a response continues to be detected (step 938). Once a response is no longer detected (step 938), the method is complete (step 940).

When the method is finished (at step 920 or step 940), the excitability threshold has been identified as somewhere between the most recent measurement at which there was no response and the most recent measurement at which there was a response. Accordingly, an excitability threshold value may be calculated as the average of the foregoing two amplitudes, or may just be taken as the lowest stimulation value that resulted in a response.

It should be noted that while the foregoing method uses a linear search technique to identify the excitability threshold, other search strategies are also possible. For example, if lower and upper bounds can be identified before the process begins, a binary search technique would be possible. For details of this method, see FIG. 15 and the accompanying description below.

As stated above, the expected baseline values used by the method (see steps 912 and 926) can be set by the patient's physician or can represent historical information. Excitability exhibits diurnal cyclical variability, and tends to vary between when the patient is sleeping and when the patient is awake. To reduce the possibility of misleading excitability measurements, any baseline value used should take into account this cyclical behavior, for example by taking a moving average of time-correlated values over the last several (e.g., five) days (or fewer if any day in that period has a previously-identified abnormal excitability measurement). There are other approaches to tracking historical excitability information that would also be expected to provide advantageous results; for example, if the device 110 (FIG. 1) includes the capability of determining whether the patient is asleep, that data might be used to index the expected excitability threshold.

Figure 10:
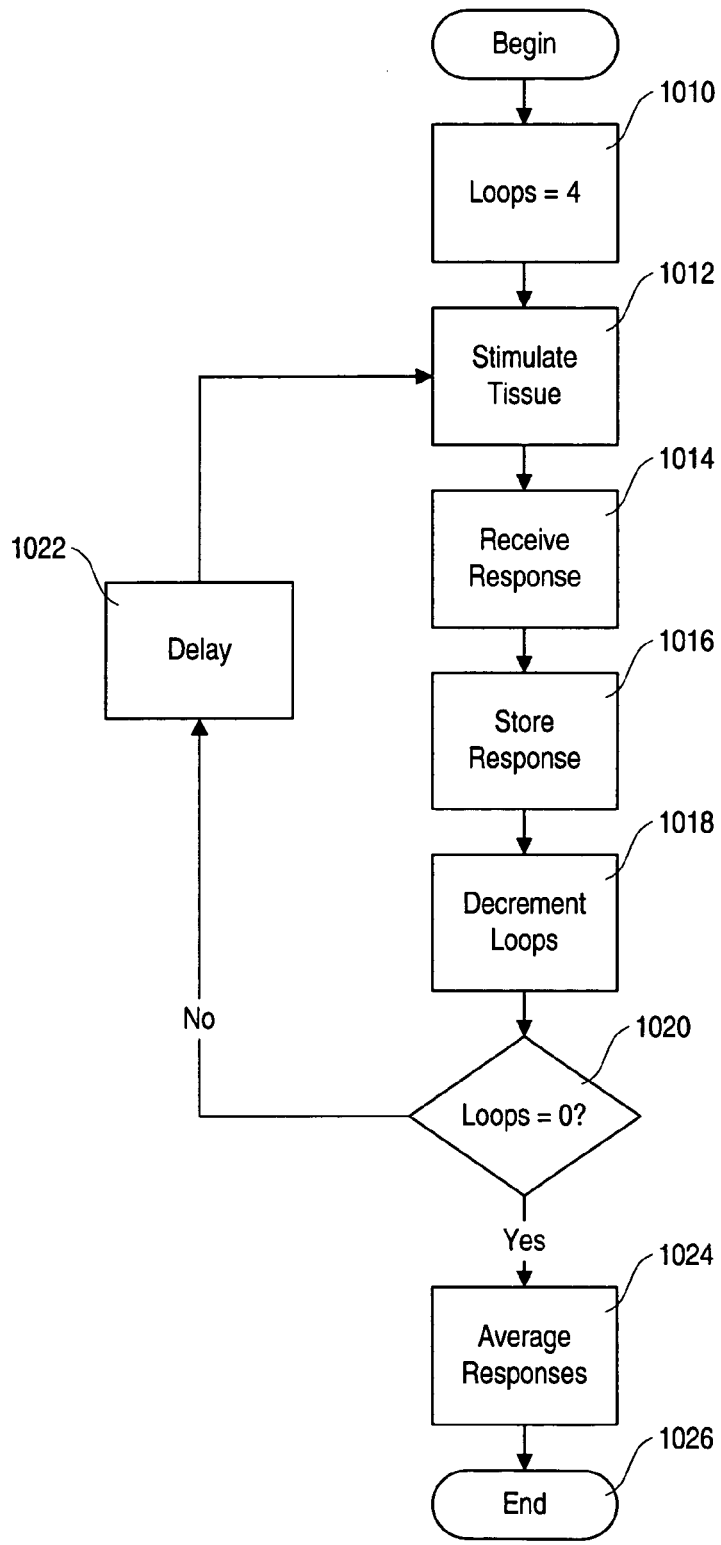
FIG. 10 is a flow chart illustrating the process performed in testing an excitability level of a bran region in a system or method according to the process of FIG. 9.

FIG. 10 illustrates the steps performed in acquiring an individual excitability measurement at a specified amplitude, as in steps 916, 928, and 936 of FIG. 9. By default, excitability is measured at the same amplitude four times in sequence and the resulting signals are summed and averaged—any evoked responses will tend to reinforce each other, while noise and other background signals contribute less to the aggregate. Accordingly, the number of remaining loops is initially set to four (step 1010). The neural tissue to be tested is then stimulated with a single pulse (preferably charge-balanced) at the selected amplitude (step 1012). In the disclosed embodiment, the charge-balanced pulse applied at this step has a constant current, and a duration of approximately 300 µs per phase (for a total duration of approximately 600 µs), but other pulse configurations are possible. It has been found to be advantageous to perform the excitability tests herein with stimulation current as the variable parameter. Voltage will vary depending on the impedance of the leads and the neurological tissue in the stimulation circuit.

Any response is then received (step 1014) and recorded (step 1016). The number of remaining loops is decremented (step 1018), and if there are any iterations remaining (step 1020), a delay is taken (step 1022) to allow any inhibitory response to diminish and the stimulation and measurement steps are performed again (steps 1012–1016). A sufficient delay is provided between each iteration to ensure that there is no inhibitory or other effect from the preceding stimulus when the next stimulus is applied. This delay may be varied according to a pattern or at random to reduce the possibility of results skewed by acclimation or long term potentiation. When all four loops have been performed (step 1020), the stored responses are averaged (step 1024) and the measurement is complete (step 1026).

As set forth above, evoked responses are separated from noise by averaging over multiple stimuli. Averaging over four loops will generally provide an acceptable signal to noise ratio for the substantially unambiguous determination of evoked responses when implanted deep brain electrodes are appropriately located and used in accordance with the invention, but it should be noted that a smaller number may be adequate, or a larger number may be necessary depending on the circumstances.

Figure 11:
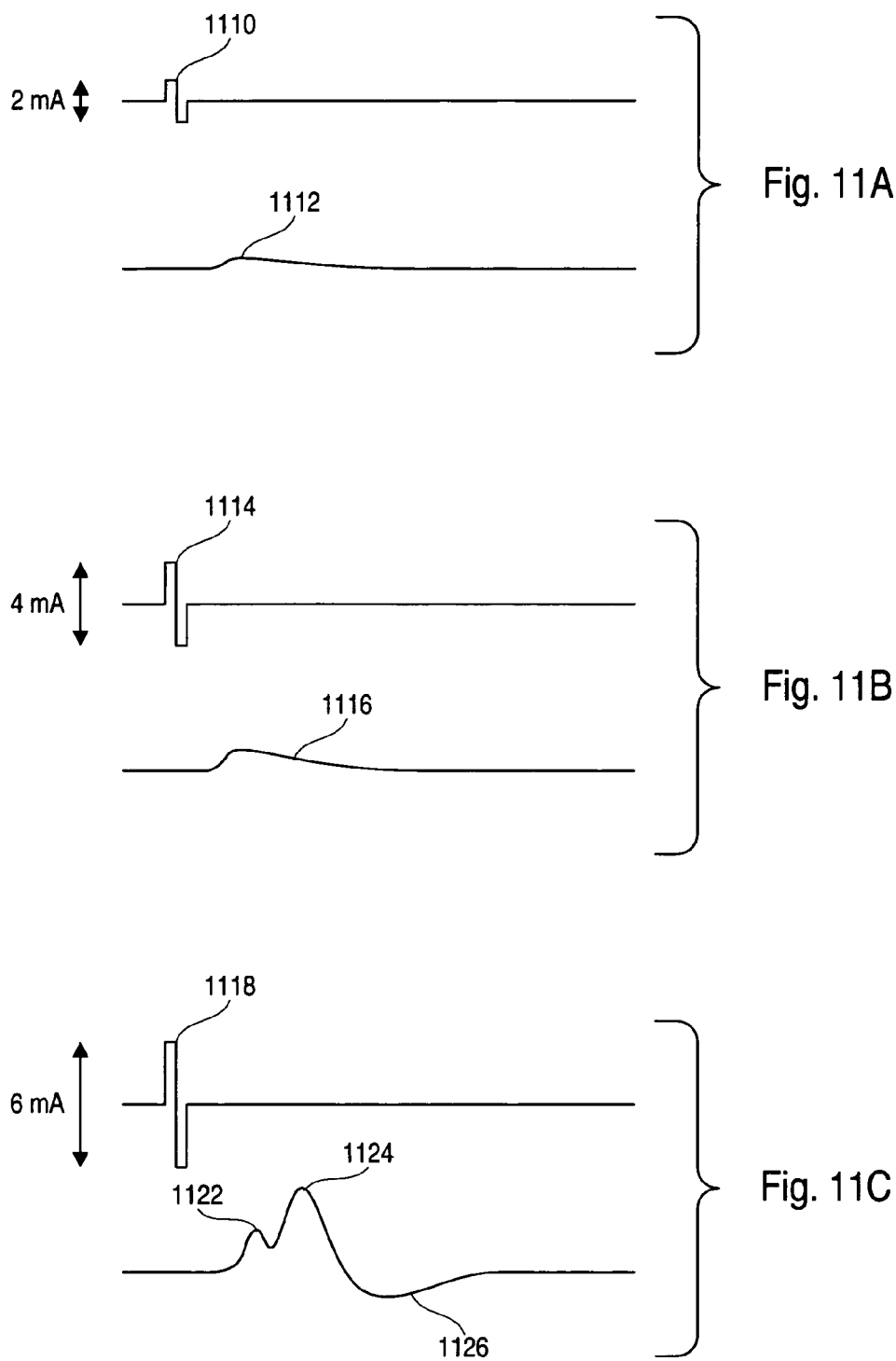
FIG. 11 sets forth three graphs illustrating representative excitability response patterns identified by the process depicted in FIG. 9.

FIG. 11 illustrates several exemplary stimulation pulses applied as described in the excitability test procedure detailed above. FIG. 11A illustrates a first stimulation signal 1110 that comprises a charge-balanced pulse having an amplitude of 2 mA; that pulse is applied to a stimulation electrode implanted at a desired stimulation site. As set forth above, in one embodiment of the invention, the stimulation electrode would be implanted in the parahippocampal gyrus (PHG) 314 (FIG. 3). In response to the stimulation pulse, a first responsive signal 1112 is received with a measurement electrode implanted at a desired measurement site, which in one embodiment of the invention is the hippocampus 312. Note that the first responsive signal 1112 (which in the figure has substantially no noise, and can be considered an average response over multiple stimuli) exhibits a relatively small deviation occurring after the first stimulation signal 1110. This deviation in the first responsive signal 1112 is very small, and does not represent a physiological response (merely a filtered transmission of the original first stimulation signal 1110), so the amplitude of 2 mA is deemed to be below the excitability threshold.

FIG. 11B illustrates a second stimulation signal 1114; this signal comprises a pulse with an amplitude of 4 mA. The second responsive signal 1116 is similar to the first responsive signal 1112, so the stimulation amplitude of 4 mA is also deemed to be below the excitability threshold.

FIG. 11C illustrates a third stimulation signal 1118; this signal comprises a pulse with an amplitude of 6 mA. The third responsive signal 1120 is of a different character than the previous two responsive signals 1116 and 1112. The third responsive signal 1120 is characterized by a first deviation 1122, a second deviation 1124, and a third deviation. The first deviation is similar to the deviations exhibited in the other two sub-threshold responsive signals 1112 and 1116, and is believed to represent a filtered transmission of the stimulation pulse. The second deviation 1124 represents an excitatory response—it is greater in amplitude than either the first deviation 1122 or any characteristic of the other responsive signals 1112 and 1116. Accordingly, the second deviation 1124 is the characteristic that identifies the third responsive signal 1120 as an evoked response, which identifies the stimulation amplitude of 6 mA as above the excitability threshold. The excitability threshold is hence between 4 mA and 6 mA, so a calculated figure of 5 mA is used for purposes of the invention. The third responsive signal 1120, as illustrated in FIG. 11C, is representative of what a certain excitatory response waveform may look like. However, note that other types of responses are also possible, which may or may not look significantly like the waveform of FIG. 11C. However, the principles set forth above should continue to apply. To identify an excitatory evoked response, it is necessary to look beyond the existence of a deviation in the responsive signal. Rather, it is necessary to identify a sufficiently large "peak" in that signal, or a non-monotonic characteristic with multiple peaks. The existence of noise in the responsive signal can complicate this analysis, but sufficient averaging should decrease the influence of noise. Note that "noise" as referred to herein does not refer solely to electromagnetic interference received from external sources—it also includes any EEG signal not directly evoked by or related to the preceding stimulus pulse. Thus, "noise" for purposes of this system and method can include, among other things, EEG signals representative of normal brain activity.

It should further be observed that the amplitudes illustrated in FIG. 11, and particularly the relationships between the amplitudes of the stimulation signals and the responsive signals, are for purposes of illustration only and are not to scale. Similarly, the signal durations and latencies are meant to be representative, and are not drawn to scale.

As set forth above, one method for determining whether a measured response is representative of an electrophysiological evoked response involves physician interaction. Before the device 110 is fully programmed, a physician causes the device 110 to perform a sequence of excitability tests at various amplitudes. The responses to those tests are stored as necessary and transmitted to the programmer 512 via the communication subsystem 634. The programmer allows the physician to view each response and visually ascertain which ones, if any, represent excitatory responses. A representative excitatory response is then selected by the physician for use as a template and transmitted back to the device 110. Accordingly, then, in the method set forth in FIGS. 9–10, each time a response is analyzed, it can be compared to the representative excitatory response to determine whether a particular response represents neural excitation. This approach is more computationally intensive, but potentially more accurate, than simply comparing each response to a threshold as described above.

This template comparison operation is preferably performed by scaling the measured response (or the template) so the measured response and the template substantially match in amplitude and duration, and thereafter quantifying any difference between the two signals. If the difference exceeds a predetermined (or programmed) threshold, then the measured response and the template do not match, and there has been no excitatory response. If the threshold is not exceeded, then the measured response and the template substantially match, indicating an excitatory response.

Template matching can be performed by comparing amplitude on a sample-by-sample basis, or preferably is accomplished by decomposing both the template and the measured response into features, such as half waves or line segments, and comparing the attributes of the appropriate features.

It should be noted that the complementary operation can also be performed. The physician can identify a representative non-excitatory response, and program that as a template. In the absence of other factors, any measured response that matches the template is also most likely non-excitatory, and any measured response that does not match the template is most likely excitatory.

Figure 12:
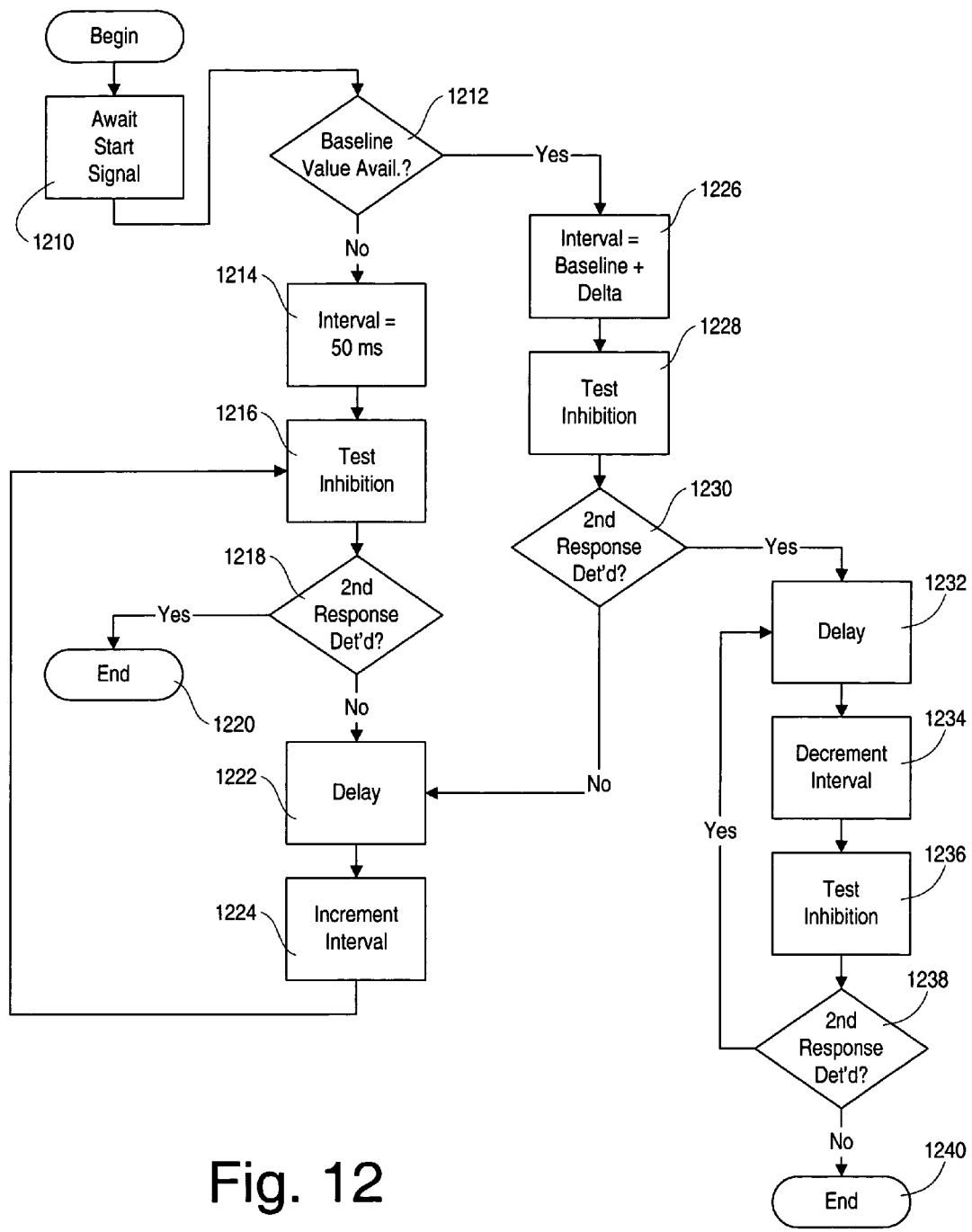
FIG. 12 is a flow chart illustrating the process performed in measuring the refractoriness of a region of a patient's brain in an embodiment of the invention.

FIG. 12 illustrates the method used to measure the refractoriness of neural tissue in a particular pathway according to the invention. As described above, "refractoriness" of a neural pathway is an indication of how long it takes the neurons in the pathway to recover from a previous stimulation. Typically, after a neural pathway is excited, it takes some time for the pathway to recover and become able to exhibit another response. The length of this post-excitation period, in which a response in the pathway is inhibited, is the refractoriness parameter desired to be measured.

Referring now to FIG. 12, the method begins by awaiting a start signal (step 1210), during which time the device 110 (FIG. 1) can be performing other operations, including other measurement, detection, and stimulation operations.

As with excitability, the baseline refractoriness value is stored in the memory subsystem 630 by the external programmer 512. Prior to programming the device 110, the patient's physician commands the device 110 (via the programmer 512) to perform a sequence of refractoriness measurements by the methods set forth below; the resulting waveforms, rather than being automatically analyzed by the device, are downloaded to the programmer 512 for consideration by the physician. The physician can then select the results most representative of an uninhibited response, and program the parameters of that response into the device for future automatic use as a baseline threshold value. This procedure can be performed several times, at various times of day, to give the physician multiple options in choosing appropriate parameters, and to account for diurnal cyclical variation in refractoriness. And again, baseline values for refractoriness can be obtained by comparing measurements in a patient's sclerotic region to measurements from non-sclerotic analogous structures in the other hemisphere, subject to the limitations set forth above with regard to excitability.

If there is no baseline refractoriness time period available (step 1212), measurement via a linear search technique begins by setting an initial inter-pulse interval to 50 ms (step 1214). The inhibition characteristics of the desired neural tissue are then tested by applying a pair of pulses with the desired inter-pulse interval (step 1216). Each pulse in the pair is of an amplitude that exceeds the excitability threshold (as determined above). The first pulse in the pair of pulses causes an excitatory evoked response; whether the second pulse causes a similar response depends on whether the inter-pulse delay exceeds an inhibition period, which is the parameter sought to be identified. Again, an excitatory response in connection with the second pulse is what the present method is intended to identify, and as above (See FIG. 11), the existence of a second deviation in a responsive signal is indicative. This measurement method will be set forth in further detail below in connection with FIGS. 13–14.

If a second excitatory response is detected (step 1218), the inhibition period has been exceeded and the method is complete (step 1220). Otherwise, a delay is taken (step 1222) to allow the stimulated tissue to recover from its inhibitory behavior, the inter-pulse interval is incremented by 50 ms (step 1222), and inhibition is tested again (step 1216). Although the initial inter-pulse interval is set to 50 ms by step 1214 and is incremented 50 ms at a time by step 1224, it should be recognized that any desired starting interval and increment value, whether or not uniform, can be used with similar results, but will change the resulting resolution and the time required to perform a measurement. Also, it would be beneficial to implement an upper bound to the incrementation performed in step 1222, in case a second response is never detected.

If a baseline inter-pulse interval is available (step 1212), there is no need to test the entire range of inhibition periods, so the initial inter-pulse interval is set to the baseline value plus a delta (step 1226). Preferably, the delta is equal to half the desired resolution (or increment value used in step 1224). The inhibition period is tested using the initial inter-pulse interval (step 1228). If a second response is not detected (step 1230), then the inter-pulse interval is shorter than the inhibition period, and after a delay (step 1222), the interval is incremented (step 1224) and inhibition is tested again (step 1216). If, on the other hand, a second response is detected (step 1230), then the inter-pulse interval exceeds the inhibition period, and after a delay (step 1232), the interval is decremented (step 1234), and inhibition is again tested (step 1236). If a second response is then detected (step 1238), the method is finished (step 1240). Otherwise, there is another delay (step 1232), and the inter-pulse interval is decremented (step 1234) and tested again (step 1236).

When the method is finished (at step 1220 or step 1240), the inhibition period has been identified as somewhere between the most recent measurement at which there was no second response and the most recent measurement at which there was a second response. Accordingly, a measured inhibition period value is calculated as the average of the preceding two measurements.

It should be noted that while the foregoing method uses a linear search technique to identify the inhibition period or refractoriness, other search strategies are also possible. For example, if lower and upper bounds can be identified before the process begins, a binary search technique would be possible. For details of this method, see FIG. 15 and the accompanying description below.

As stated above, the expected baseline values used by the method (see steps 1212 and 1226) can be set by the patient's physician or can represent historical information. Like excitability, it is believed that refractoriness may exhibit diurnal cyclical variability. To reduce the possibility of misleading inhibition period measurements, any baseline value used should take into account this cyclical behavior, for example by taking a moving average of time-correlated values over the last several (e.g., five) days (or fewer if any day in that period has a previously-identified abnormal measurement). And as above, there are other approaches to tracking historical inhibition information that would also be expected to provide advantageous results; for example, if the device 110 (FIG. 1) includes the capability of determining whether the patient is asleep, that data might be used to index the expected baseline inhibition period.

Figure 13:
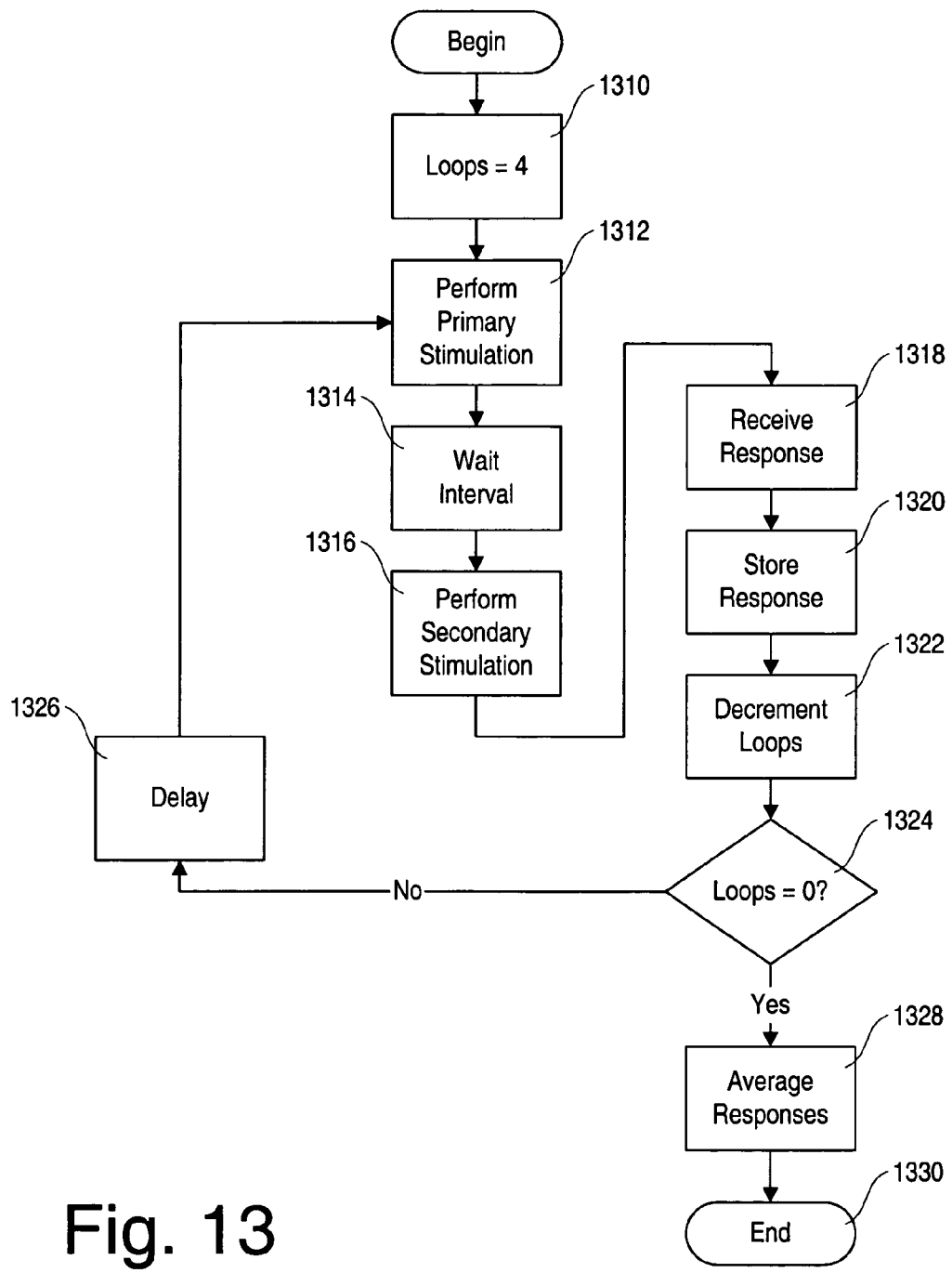
FIG. 13 is a flow chart illustrating the process performed in testing an inhibition level of a brain region in a system or method according to the process of FIG. 12.

As indicated above, FIG. 13 illustrates the method performed in taking a single measurement of the inhibition period of neurological tissue at a desired inter-pulse interval, as in steps 1216, 1228, and 1236 of FIG. 12. As with the excitability measurements described above, four iterations are performed to provide sufficient signal to noise ratio for the substantially unambiguous identification of evoked responses.

The method begins by setting a loop counter to four (step 1310). A primary charge-balanced stimulation pulse is then applied (step 1312). Preferably, the primary stimulation pulse has an amplitude sufficient to evoke an excitatory response (as determined above, or as previously programmed), and a known duration (e.g., 300 µs per phase, as above). The response to this pulse is not preserved. A delay corresponding to the desired inter-pulse interval is then observed (step 1314), and a secondary charge-balanced stimulation pulse is applied (step 1316). The secondary stimulation pulse preferably has parameters substantially equal to those of the primary stimulation pulse. Any evoked response is then received (step 1318) and stored (step 1320). The loop counter is decremented (step 1322), and if there are any iterations remaining (step 1324), a delay sufficient to reduce any remaining inhibitory response is performed (step 1326). As above, a sufficient delay is provided between each iteration to ensure that there is no inhibitory or other effect from the preceding stimulus when the next stimulus is applied. This delay may be varied according to a pattern or at random to reduce the possibility of results skewed by acclimation or long term potentiation. When all four loops have been performed (step 1324), the stored responses are averaged (step 1328) and the measurement is complete (step 1330).

Figure 14:
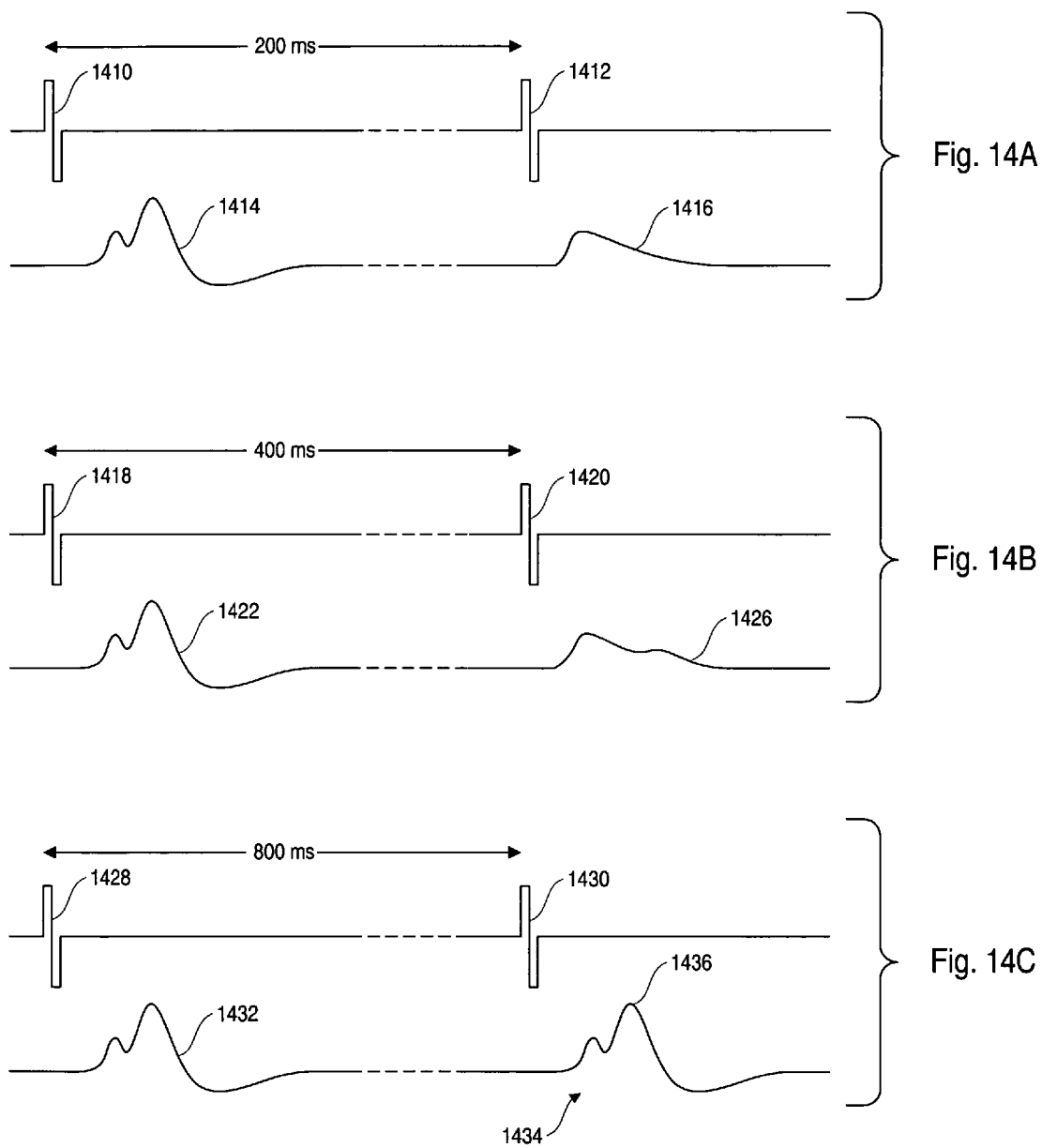
FIG. 14 sets forth three graphs illustrating representative refractoriness response patterns identified by the process depicted in FIG. 11.

FIG. 14 illustrates representative waveforms potentially observed in several inhibition period measurements performed according to the method of FIG. 13. Referring initially to FIG. 14A, a primary stimulation pulse 1410 (having an amplitude sufficient to evoke an excitatory response) is applied to a stimulation electrode implanted at a stimulation site, followed after an inter-pulse delay of 200 ms by a secondary stimulation pulse 1412 applied to the same stimulation site. A primary response 1414, representative of excitation, is received at a sensing electrode implanted at a measurement site after the primary stimulation pulse 1410, and a secondary response 1416 is received at the sensing electrode after the secondary stimulation pulse 1412. Like the responses illustrated in FIGS. 11A and 11B, the secondary response 1416 is not representative of a physiological evoked response, only a filtered transmission of the secondary stimulation pulse 1412. Accordingly, the inter-pulse delay of 200 ms is shorter than the inhibition period, and the secondary response 1416 has been inhibited.

A similar situation is illustrated in FIG. 14B. A primary stimulation pulse 1418 is applied, followed by a secondary stimulation pulse 1420 after an inter-pulse delay of 400 ms. A primary response 1422 is excitatory, but the secondary response 1424 is primarily inhibited. Note that there is a small second deviation 1426 illustrated in the secondary response 1424 of FIG. 14B, indicating that the secondary response does have a small (but insignificant at this point) evoked component.

In FIG. 14C, a primary stimulation pulse 1428 is followed by a secondary stimulation pulse 1430 after an inter-pulse delay of 800 ms. Both the primary response 1432 and the secondary response 1434 are excitatory, indicating that the inhibition period has been exceeded by the inter-pulse interval. A substantial second deviation 1436 in the secondary response 1434 is indicative of the excitatory response. Although the second deviation 1436 is indicative in this instance, it should be noted that other characteristic responses are possible in various circumstances. The form of an excitatory response may vary depending on the neural pathway or the type of neural tissue being examined, among numerous other factors. In any event, there is expected to be a signal perturbation adequate for analysis and identification by an implanted self-contained measurement system according to the invention.

It should again be observed that the amplitudes illustrated in FIG. 14, and particularly the relationships between the amplitudes of the stimulation signals and the responsive signals, are for purposes of illustration only and are not to scale. Similarly, the signal durations, delays, and latencies are meant to be representative, and are not drawn to scale.

As described above, a method for determining whether a measured response is representative of an electrophysiological evoked response involves physician interaction. Before the device 110 is fully programmed, a physician causes the device 110 to perform a sequence of refractoriness tests at various inter-pulse intervals. The responses to those tests are stored as necessary and transmitted to an external apparatus via the communication subsystem 634. The external apparatus, which preferably is a programmer adapted to receive and display information from the device 110, allows the physician to view each response and visually ascertain which ones, if any, represent uninhibited responses. A representative uninhibited response is then selected by the physician for use as a template and transmitted back to the device 110. Accordingly, then, in the method set forth in FIGS. 12–13, each time a response is analyzed, it can be compared to the representative uninhibited response to determine whether a particular response represents inhibition.

As above, the template comparison operation is preferably performed by scaling the measured response (or the template) so the measured response and the template substantially match in amplitude and duration, and thereafter quantifying any difference between the two signals. If the difference exceeds a predetermined (or programmed) threshold, then the measured response and the template do not match, and there has been no uninhibited response. If the threshold is not exceeded, then the measured response and the template substantially match, indicating an uninhibited response.

Template matching can be performed by comparing amplitude on a sample-by-sample basis, or preferably is accomplished by decomposing both the template and the measured response into features, such as half waves or line segments, and comparing the attributes of the appropriate features.

It should be noted that a complementary operation can also be performed. The physician can identify a representative inhibitory response, and program that as a template. In the absence of other contributing factors, any measured response that matches the template is also most likely inhibitory, and any measured response that does not match the template is most likely uninhibited.

Note that for this measurement and also for excitability, multiple templates can be used to address different electrode combinations or different expected baselines (e.g., depending on the time of day). However, if most or all expected responses are similar in their features, it should be observed that multiple templates need not be used; a generalized template can be created by the physician via the programmer and used in multiple electrophysiological parameter measurement scenarios.

Figure 15:
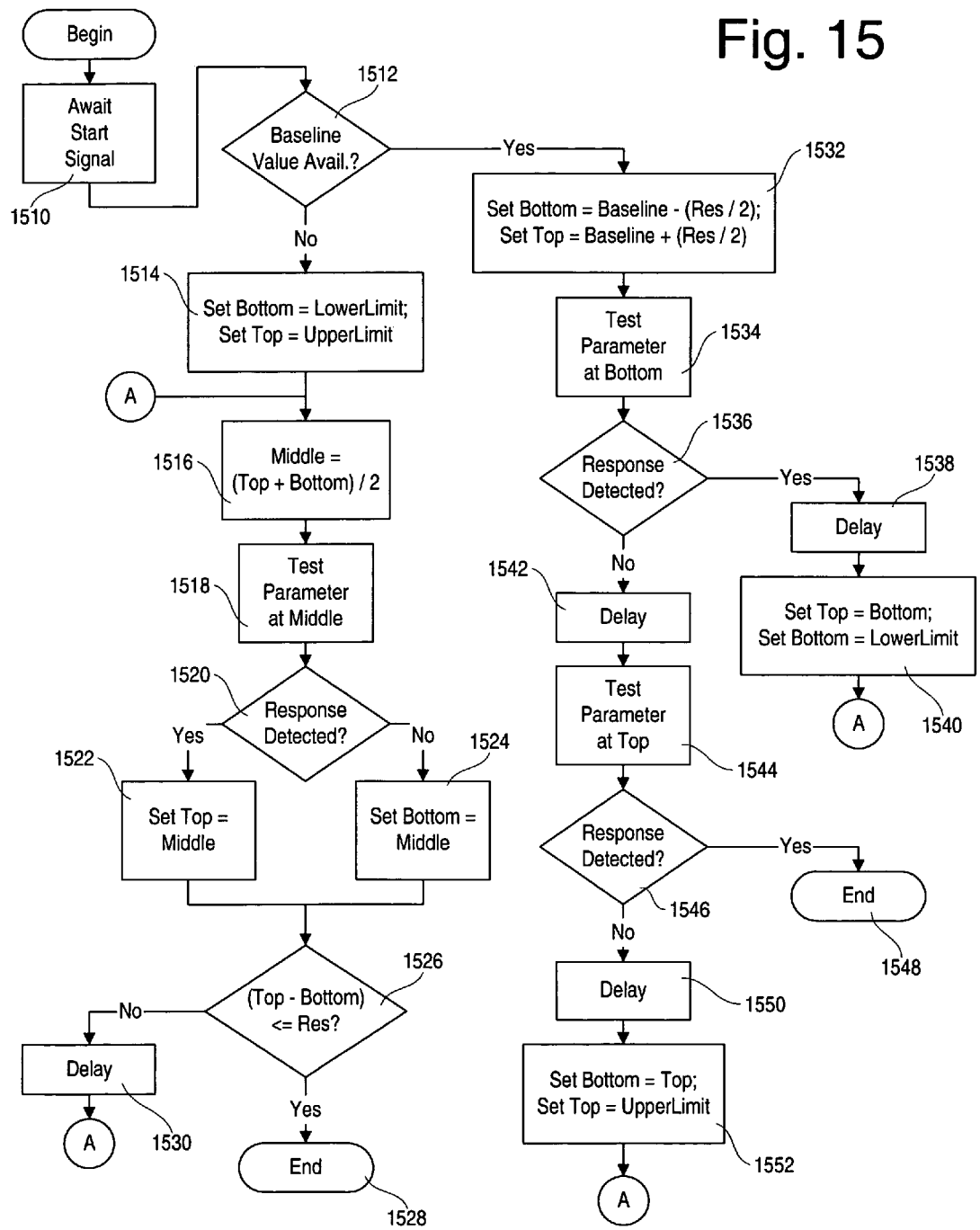
FIG. 15 is a flow chart illustrating the process performed in measuring an electrophysiological parameter in a patient's brain using a binary search method.

As described above, the simplest method for identifying the excitability of refractoriness of neural tissue involves a linear search for the correct results. Depending on the circumstances, however, it may be advantageous to use a binary search strategy. Such an approach is illustrated in FIG. 15.

To test excitability with the binary search strategy, FIG. 15 proceeds as follows. The method begins, once again, by awaiting a start signal (step 1510), during which time other functions can be performed by the device 110 (FIG. 1). The memory subsystem 630 (FIG. 6) is queried for the existence of a baseline excitability value (step 1512), which in the disclosed embodiment is stored in the memory subsystem 630 after having been received from the programmer 512 (FIG. 5). If one is not available, the method proceeds by selecting appropriate lower and upper bounds, and setting a range bottom and a range top accordingly (step 1514). For purposes of testing excitability according to the invention, it may be appropriate to set the range bottom to 1 mA and the range top to 10 mA. The middle point is then calculated as an arithmetic average of the range top and the range bottom (step 1516); this average middle point is then used as the amplitude for performing the excitability test (in the same manner illustrated in FIG. 10), and accordingly, the excitability is tested (step 1518) at the middle.

If an excitatory response is detected (step 1520), the excitability threshold must be in the lower half of the range, so the range bounds are adjusted so the new range top is equal to the tested middle point (step 1522). If no excitatory response is detected (step 1520), the excitability threshold must be in the upper half of the range, so the range bounds are adjusted so the new range bottom is equal to the tested middle point (step 1524). The difference between the range bottom and the range top is tested to determine whether it is smaller than a desired resolution (step 1526). If so, the measured excitability threshold is deemed to be the middle of the range and the process is finished (step 1528). Otherwise, a delay is performed to eliminate any lingering inhibitory or other effects (step 1530), a new middle point is calculated (step 1516) and the process continues.

If there is a baseline excitability value available (step 1512), there is no need to test the entire range of excitability values; instead, the testing range is defined to accommodate it. The range bottom is defined to be the baseline value minus half of the desired resolution, and the range top is defined to be the baseline value plus half of the desired resolution (step 1532). Accordingly, if the excitability threshold is determined to be within this range, no further testing need be performed. So the excitability is first tested at the range bottom (step 1534).

If there is a response detected, then the excitability threshold is somewhere below the current range bottom, so after a delay to allow any remaining inhibitory response to diminish (step 1538), a new range top is set to the tested range bottom (which was determine to be higher than the threshold), and a new range bottom is set to the lower limit, in the disclosed embodiment 1 mA. A new midpoint is then calculated (step 1516) and the binary search continues.

If no response was detected, a delay is performed (step 1542), and excitability is tested at the top of the existing range (step 1544). If a response is detected (step 1546), then the excitability threshold is deemed to be halfway between the bottom of the range and the top of the range, and the resolution requirement has been met, so the measurement is finished (step 1548). Otherwise, the excitability threshold must be greater than the top of the existing range. So another delay is performed (step 1550), the range is adjusted (step 1552) so the new range bottom is equal to the existing range top, and a new range bottom is set to the upper limit, which in the disclosed embodiment is 10 mA. A new midpoint is selected (step 1516), and the binary search continues.

A similar process is performed for refractoriness. A start signal is awaited (step 1510), during which time other functions can be performed by the device 110 (FIG. 1). The memory subsystem 630 (FIG. 6) is queried for the existence of a baseline inhibition period value (step 1512). If one is not available, the method proceeds by selecting appropriate lower and upper bounds, and setting a range bottom and a range top accordingly (step 1514). For purposes of testing refractoriness according to the invention, it may be appropriate to set the range bottom to 50 ms and the range top to 2000 ms. The middle point is then calculated as an arithmetic average of the range top and the range bottom (step 1516); this average middle point is then used as the interpulse interval for performing the refractoriness test (in the same manner illustrated in FIG. 13), and accordingly, the inhibition period is tested (step 1518) at the middle.

If a second response is detected (step 1520), the actual inhibition period must be in the lower half of the range, so the range bounds are adjusted so the new range top is equal to the tested middle point (step 1522). If no second response is detected (step 1520), the inhibition period must be in the upper half of the range, so the range bounds are adjusted so the new range bottom is equal to the tested middle point (step 1524). The difference between the range bottom and the range top is tested to determine whether it is smaller than a desired resolution (step 1526). If so, the measured inhibition period is deemed to be the middle of the range and the process is finished (step 1528). Otherwise, a delay is performed to eliminate any lingering inhibitory or other effects (step 1530), a new middle point is calculated (step 1516) and the process continues.

If there is a baseline refractoriness value (inhibition period) available (step 1512), there is no need to test the entire range of inhibition periods; instead, the testing range is defined to accommodate the expectation. The range bottom is defined to be the baseline value minus half of the desired resolution, and the range top is defined to be the baseline value plus half of the desired resolution (step 1532). Accordingly, if the inhibition period is determined to be within this range, no further testing need be performed.

So the inhibition is first tested at the range bottom (step 1534). If there is a second response detected, then the inhibition period is somewhere below the current range bottom, so after a delay to allow any remaining inhibitory response to diminish (step 1538), a new range top is set to the tested range bottom (which was determine to be longer than the inhibition period), and a new range bottom is set to the lower limit, in the disclosed embodiment 50 ms. A new midpoint is then calculated (step 1516) and the binary search continues.

If no response was detected, a delay is performed (step 1542), and inhibition is tested at the top of the existing range (step 1544). If a second response is detected (step 1546), then the actual inhibition period is deemed to be halfway between the bottom of the range and the top of the range, and the resolution requirement has been met, so the measurement is finished (step 1548). Otherwise, the inhibition period must be longer than the top of the existing range. So another delay is performed (step 1550), the range is adjusted (step 1552) so the new range bottom is equal to the existing range top, and a new range bottom is set to the upper limit, which in the disclosed embodiment is 2000 ms. A new midpoint is selected (step 1516), and the binary search continues.

It should be noted that the method described with reference to FIG. 15 exhibits anomalous behavior if the sought-after behavior is never identified (e.g., if no excitatory response or second response is detected). The measured value will always be the upper bound minus half of the final range size (the final range size being less than or equal to the desired resolution), as the process terminates once the resolution requirement has been satisfied.

In an alternative embodiment of the invention, it is possible to combine the method set forth in FIG. 15 with the linear methods described in FIGS. 9 and 12. For example, it is possible to establish baseline values using linear search approach, with subsequent analysis performed using the binary method.

The foregoing binary search strategy refines the tested ranges using an arithmetic midpoint between the bottom and the top. It should be noted, however, that alternative techniques are available for selecting a "midpoint" (or analogous point) for further testing. For example, it may be advantageous to use an exponential or a logarithmic function to define the search ranges. In such a case, it may further be useful to employ a resolution criterion that is somehow dependent on the magnitude being measured (e.g., requiring greater resolution and greater precision at the bottom end of the range).

Methods for employing the excitability and refractoriness information measured by a system or method according to the invention are set forth below in connection with FIGS. 16 and 17.

Figure 16:
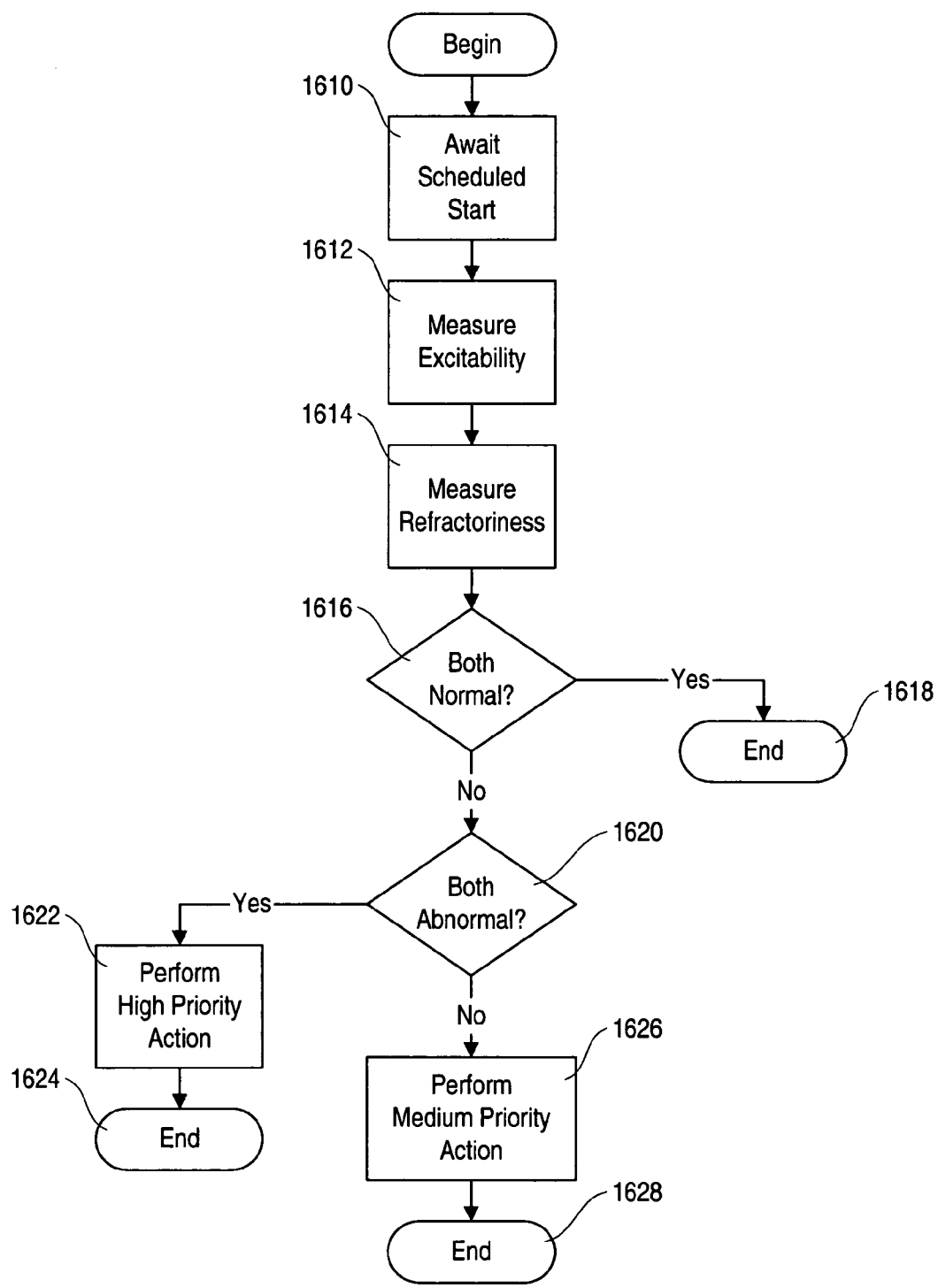
FIG. 16 is a flow chart illustrating a process by which excitability and refractoriness parameters can be used in determining whether to apply responsive treatment in a system and method according to the invention.

Referring now to FIG. 16, a method is set forth for employing the excitability and refractoriness parameters calculated above (by the methods illustrated in FIGS. 9–10 and 12–13). This method employs periodic measurement of both parameters to determine whether to perform certain actions.

The method begins by awaiting a scheduled start of an electrophysiological parameter measurement session (step 1610). Parameters may be measured periodically, or when some other operation of the device 110 (e.g., a detection that the patient is awake) or a command from the programmer 512 (FIG. 5) prompts it. It is contemplated that measurement schedules can be programmed in the device 110 by the programmer 512 via the communication subsystem 634. Measurements can be scheduled at particular times of day, after certain time delays, or on a weekly basis. In the disclosed embodiment, measurement is performed several times each day at times when the patient is awake.

The method then measures excitability (step 1612) by the method set forth above in connection with FIG. 9, and also measures refractoriness (step 1614) by the method of FIG. 12. As illustrated in FIG. 4, a single stimulation electrode is used in conjunction with a single measurement electrode; however, it should be noted that if multiple electrodes are implanted (with multiple stimulation sites and multiple measurement sites available), a number of excitability (step 1612) and refractoriness (step 1614) measurements can be taken, as desired.

If both excitability and refractoriness values are normal (step 1616); that is, within the range of expected values based on historical measurements or programmed baseline values, depending on the time of day, patient's sleep state, or other circumstances, then no special action is taken and the measurement session is finished (step 1618).

If both excitability and refractoriness values are abnormal (step 1620), that is, outside of the range of expected values, then a high priority action is taken (step 1622) perhaps even before the measurement session is finished (step 1624). Examples of high priority actions include providing an audio warning (or other sensory stimulus) to the patient to recommend that the patient take medicine, stop performing dangerous activities such as driving, or perform other tasks; initiating therapeutic electrical stimulation; administering drug therapy via an implanted drug pump; or commencing recording all EEG signals; there are also other possibilities that will be apparent.

If either excitability or refractoriness is out of the normal range, but the other is not, a medium priority action may be taken (step 1626) before the measurement session is finished (step 1628). Examples of medium priority actions include providing an audio announcement to the patient suggesting that he or she take medicine or be examined by a physician; initiating low-level continuous electrical stimulation (to the thalamus, for example) for a period of time; and recording some EEG signals; other possibilities will be apparent.

Once medium priority (step 1626) or high priority (step 1622) actions are taken, it is appropriate to once again measure the electrophysiological parameters to determine whether any applied treatment has successfully reversed the abnormal excitability or refractoriness measurements. If not, further treatment actions can be taken.

A table illustrating the actions performed in the method of FIG. 16 under various combinations of excitability and refractoriness measurements is set forth in Table 1.

TABLE 1

| Excitability | Refractoriness | |
|---|---|---|
| | Normal | Abnormal |
| Normal | No Action | Med. Priority Action |
| Abnormal | Med. Priority Action | High Priority Action |

Figure 17:
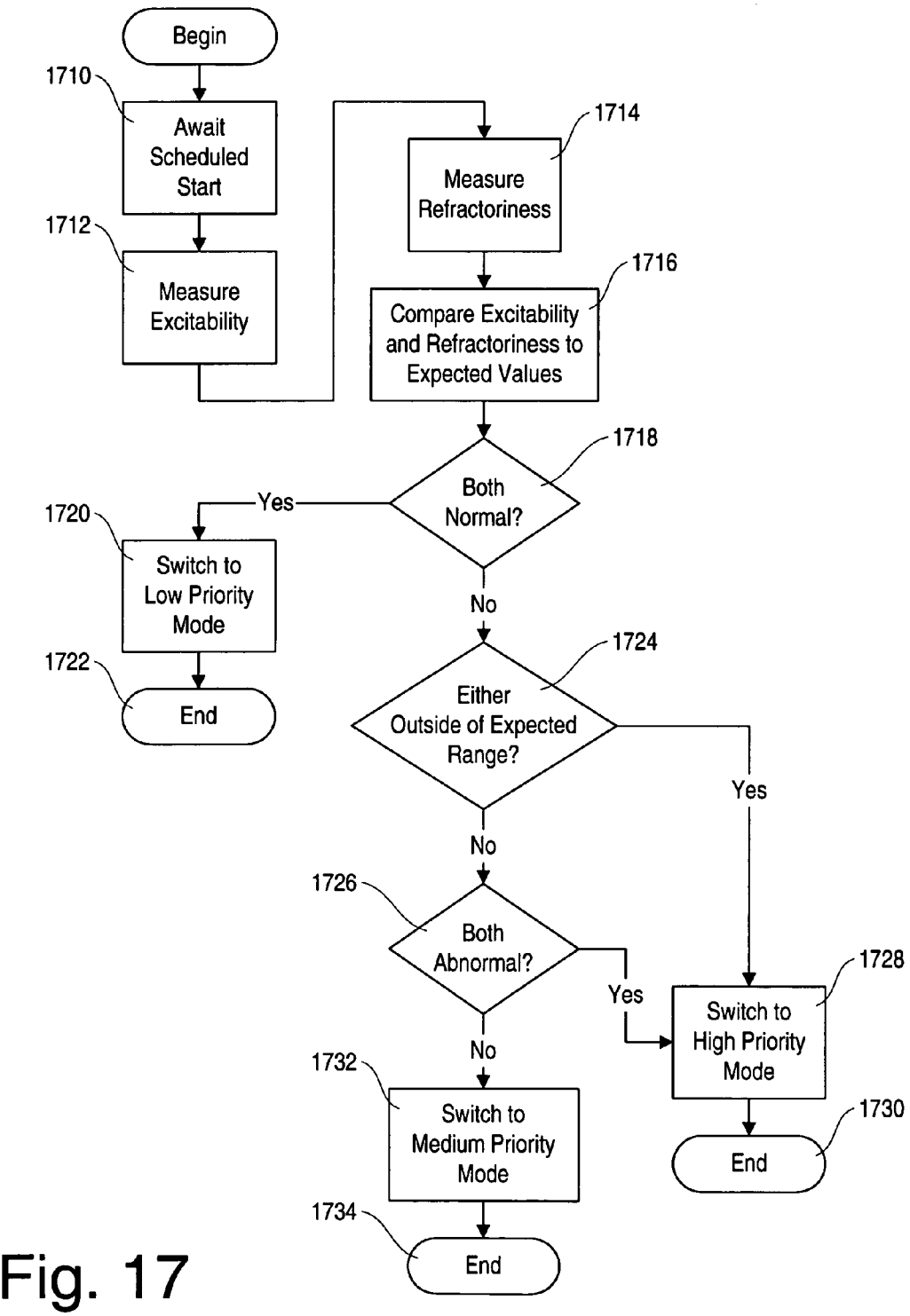
FIG. 17 is a flow chart illustrating a process by which excitability and refractoriness parameters, and short-term trends therein, can be used to control the mode of an implantable neurostimulator according to the invention.

FIG. 17 illustrates an alternative method of using the measured electrophysiological parameters to adjust a mode of the device 110 (FIG. 1). As in FIG. 16, the method begins by awaiting a scheduled start (step 1710) or a command from the programmer 512. Excitability (step 1712) and refractoriness (step 1714) are measured and compared to expected values (step 1716). If both parameters are within the range of expected values (step 1718), as described above in connection with FIG. 16, then the device 110 is switched into a low priority mode (step 1720) and the measurement session is finished (step 1722). While in low priority mode, the device 110 may take fewer measurements of electrophysiological parameters, perform fewer power-consuming analyses, or otherwise operate in a low-power state.

If either excitability or refractoriness is out of the expected range (step 1724), then the device is switched into a high priority mode (step 1728) and the method is complete (step 1730). While in high priority mode, the device 110 may take a greater number of measurements of electrophysiological parameters, may provide continuous or semi-continuous therapeutic stimulation, or may perform more computationally intensive EEG analysis algorithms, among numerous other options. It is expected that the functions performed in high priority mode will be significantly more power consuming than the functions performed in low priority mode; it is advantageous to switch into this mode despite the power consumption because the patient is believed to have a high risk of seizure activity.

If neither parameter is very far out of the expected range (step 1724) and only one of the parameters is abnormal (step 1726), then the device is switched into a medium priority mode (step 1732) before finishing (step 1734). In this mode, which is contemplated to be a compromise between the high priority mode and the low priority mode, some additional functions (beyond those performed in the low priority mode) may be performed, but not everything that leads to the high power consumption of the high priority mode. When either excitability or refractoriness is abnormal, the physician may instruct the implanted device that the patient is to be considered to be in a slightly higher likelihood of seizure activity.

As stated above, once the device is in medium priority mode (step 1732) or high priority mode (step 1728) actions are taken, it is generally appropriate to measure the electrophysiological parameters more frequently to determine whether any applied treatment is successfully reversing the abnormal excitability or refractoriness measurements. If not, further treatment actions can be taken. A table illustrating the actions performed in the method of FIG. 17 under various combinations of excitability and refractoriness measurements is set forth in Table 2.

TABLE 2

| Excitability | Refractoriness | | |
| --- | --- | --- | --- |
| | Normal | Abnormal | Out of Range |
| Normal | Low Priority Mode | Med. Priority Mode | High Priority Mode |
| Abnormal | Med. Priority Mode | High Priority Mode | High Priority Mode |
| Out of Range | High Priority Mode | High Priority Mode | High Priority Mode |

It should be observed that while the foregoing detailed description of various embodiments of the present invention is set forth in some detail, the invention is not limited to those details and an implantable neurostimulator or neurological disorder detection device made according to the invention can differ from the disclosed embodiments in numerous ways. In particular, it will be appreciated that embodiments of the present invention may be employed in many different applications to detect anomalous neurological characteristics in at least one portion of a patient's brain. It will be appreciated that the functions disclosed herein as being performed by hardware and software, respectively, may be performed differently in an alternative embodiment. It should be further noted that functional distinctions are made above for purposes of explanation and clarity; structural distinctions in a system or method according to the invention may not be drawn along the same boundaries. Hence, the appropriate scope hereof is deemed to be in accordance with the claims as set forth below.

What is claimed is:

1. A system for actively measuring at least one electrophysiological parameter of a region of a patient's brain and perform an action in response thereto, wherein the electrophysiological parameter comprises an excitability threshold of a neural pathway, the system comprising:
   a stimulation subsystem operative to apply an electrical stimulation signal to the region of the patient's brain;
   a sensing subsystem operative to detect an evoked response to the electrical stimulation signal;
   a processor operative to calculate the electrophysiological parameter based on the evoked response and to initiate an action in response to the calculated electrophysiological parameter; and
   a control module including the stimulation subsystem, the sensing subsystem, and the processor, wherein the control module has a biocompatible housing.

2. The system of claim 1, wherein the housing is implanted in the head of the patient.

3. The system of claim 2, wherein the housing is implanted intracranially.

4. The system of claim 1, further comprising a stimulation lead having at least one stimulation electrode adapted to be implanted at a first location within the region of the patient's brain.

5. The system of claim 4, further comprising a measurement lead having at least one measurement electrode adapted to be implanted at a second location within the region of the patient's brain.

6. The system of claim 1, wherein the stimulation subsystem is further operative to provide therapeutic stimulation.

7. The system of claim 1, wherein the stimulation subsystem is further operative to provide sensory stimulation.

8. A method for actively measuring an electrophysiological parameter of a region of a patient's brain, wherein the electrophysiological parameter comprises an excitability threshold of a neural pathway, the method comprising the steps of:
   selecting a test value for the electrophysiological parameter;
   performing a measurement using the test value of the electrophysiological parameter to receive a response; and
   determining whether the response meets a criterion, and if not, adjusting the test value and repeating the testing and determining steps.

9. The method of claim 8, wherein the performing step comprises the steps of:
   applying an electrical stimulation pulse to a stimulation lead implanted in a first location in the region of the patient's brain; and
   receiving a response signal with a measurement lead implanted in a second location in the region of the patient's brain.

10. The method of claim 9, wherein the determining step comprises identifying an evoked response in the response signal.

11. The method of claim 9, further comprising the steps of;
   repeating the applying and receiving steps at least once;
   averaging the response signals to produce an average response signal.

12. The method of claim 8, wherein the adjusting step employs a linear search strategy.

13. The method of claim 8, wherein the adjusting step employs a binary search strategy.

14. The method of claim 8 further comprising the step of calculating the electrophysiological parameter if the response meets the criterion.

15. The method of claim 14, further comprising the step of performing an action in response to the calculated electrophysiological parameter.

16. The method of claim 15, wherein the step of performing an action comprises applying therapeutic electrical stimulation to a location in the patient's brain.

17. The method of claim 15, wherein the step of performing an action comprises providing a warning to the patient.

* * * * *